(12) United States Patent
Thormann

(10) Patent No.: US 7,705,037 B2
(45) Date of Patent: Apr. 27, 2010

(54) 1-SUBSTITUTED PYRROLIDIN-2-ONES AND USE THEREOF AS PEPTIDE DEFORMYLASE INHIBITORS

(75) Inventor: Michael Thormann, Martinsried (DE)

(73) Assignee: Novartis AG, Basel (CH)

( * ) Notice: Subject to any disclaimer, the term of this patent is extended or adjusted under 35 U.S.C. 154(b) by 2 days.

(21) Appl. No.: 11/916,618

(22) PCT Filed: Jun. 6, 2006

(86) PCT No.: PCT/EP2006/005369

§ 371 (c)(1),
(2), (4) Date: Dec. 5, 2007

(87) PCT Pub. No.: WO2006/131303

PCT Pub. Date: Dec. 14, 2006

(65) Prior Publication Data

US 2008/0207686 A1 Aug. 28, 2008

(30) Foreign Application Priority Data

Jun. 7, 2005 (DE) ................ 10 2005 026 232

(51) Int. Cl.
*A01N 43/36* (2006.01)
(52) U.S. Cl. ............... 514/425; 514/424; 514/429; 548/543; 548/544
(58) Field of Classification Search ............... 514/425, 514/429, 424; 548/543, 544
See application file for complete search history.

(56) References Cited

FOREIGN PATENT DOCUMENTS

WO 01/44179 A1 6/2001
WO 02/102790 A1 12/2002

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Clarke et al., "The Action of Formaldehyde on Amines and Amino Acids," Journal of the American Chemical Society 55(11):4571-4587 (1933).

* cited by examiner

*Primary Examiner*—Kamal A Saeed
*Assistant Examiner*—Valerie Rodriguez-Garcia
(74) *Attorney, Agent, or Firm*—John Alexander

(57) ABSTRACT

The present invention relates to compounds of formula (I).

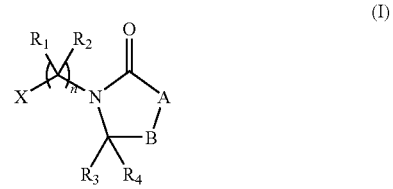

These compounds are a novel type of peptide deformylase (PDF) inhibitors, and are therefore of great interest especially as new antibiotics.

10 Claims, No Drawings

1-SUBSTITUTED PYRROLIDIN-2-ONES AND USE THEREOF AS PEPTIDE DEFORMYLASE INHIBITORS

This application is a U.S. National Phase filing of PCT/EP2006/005369 filed Jun. 6, 2006, the contents of which are incorporated herein by reference.

The present invention relates to new inhibitors of peptide deformylase (PDF). These compounds are of great interest in particular as antibiotics.

Peptide deformylase is a bacterial metalloenzyme which contains iron. It is detectable in all bacteria and plays a vital role in bacterial metabolism. During protein synthesis, peptide deformylase catalyses the removal of the formyl group from the N-terminus of bacterial proteins. Without the enzyme, bacteria cannot produce any functioning proteins. Peptide deformylase is the point of application of a new class of antibiotics, which are called peptide deformylase inhibitors.

It is the aim of the present invention to prepare new inhibitors of peptide deformylase that are obtainable synthetically in a simple manner.

The present invention relates to compounds of formula (I),

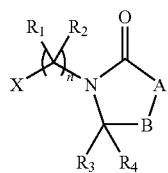

(I)

wherein
the radicals $R_1$ and $R_2$, independently of one another, are a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical; and $R_3$ is a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical;

$R^4$ is a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical;

n is equal to 1 or 2;

A—B together is a group of formula —CO—CR$_5$R$_7$— or —C(OR$_6$)=CR$_5$—.

$R_5$ is a hydrogen atom, a halogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical;

$R_6$ is a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical;

$R_7$ is a hydrogen atom, or an alkyl, alkenyl, alkinyl, heteroalkyl, aryl, heteroaryl, cycloalkyl, alkylcycloalkyl, heteroalkylcycloalkyl, heterocycloalkyl, aralkyl or heteroaralkyl radical; and X is a group of formula Formel —CH$_2$—NOH—CHS, —NOH—CHS, —NOH—CHO, —CH$_2$—NOH—CHO, —CH$_2$—CHOH—CHO, —CHOH—CHO, —COOH or —CH$_2$COOH or is selected from the following formulae:

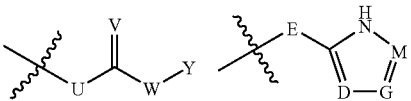

whereby U is a bond, CH$_2$, NH, O or S, V is O, S, NH or CH$_2$, W is O, S, NH or CH$_2$, and Y is OH or NH$_2$, E is a bond, CH$_2$, NH, O or S and the groups D, G and M, independently of one another, are N or CH, whereby compounds of formula (I), in which $R_5$ or $R_7$ is a group of formula —Q(=O)—R$_8$ are excluded, whereby Q is a sulfur atom, a carbon atom or a S=O group, and $R_8$ is a hydrogen atom, a halogen atom, an alkyl, alkenyl, alkinyl, heteroalkyl, aryl, heteroaryl, cycloalkyl, alkylcycloalkyl, heteroalkylcycloalkyl, heterocycloalkyl, aralkyl or a heteroaralkyl radical;

whereby all the above radicals may optionally be substituted, or a pharmaceutically acceptable salt, solvate, hydrate or pharmaceutically acceptable formulation thereof.

The expression alkyl refers to a saturated, straight-chained or branched hydrocarbon group, which has in particular 1 to 20 carbon atoms, preferably 1 to 12 carbon atoms, most preferably 1 to 6 carbon atoms, e.g. the methyl, ethyl, propyl, isopropyl, n-butyl, isobutyl, tert-butyl, n-hexyl, 2,2-dimethylbutyl or n-octyl group.

The expressions alkenyl and alkinyl refer to at least partly unsaturated, straight-chained or branched hydrocarbon groups, which have in particular 2 to 20 carbon atoms, preferably 2 to 12 carbon atoms, most preferably 2 to 6 carbon atoms, e.g. the ethenyl, allyl, acetylenyl, propargyl, isoprenyl or hex-2-enyl group. Alkenyl groups preferably have one or two (most preferably one) double bond(s) and the alkinyl groups have one or two (most preferably one) triple bond(s).

In addition, the expressions alkyl, alkenyl and alkinyl refer to groups, in which e.g. one or more hydrogen atoms are replaced by a halogen atom (preferably F or Cl), —COOH, —OH, —SH, —NH$_2$, —NO$_2$, =O, =S, =NH, such as the 2,2,2-trichloroethyl or the trifluoromethyl group.

The expression heteroalkyl refers to an alkyl, alkenyl or alkinyl group, in which one or more (preferably 1, 2 or 3) carbon atoms are replaced by an oxygen, nitrogen, phosphorus, boron, selenium, silicon or sulfur atom (preferably oxygen, sulfur or nitrogen). The expression heteroalkyl refers furthermore to a carboxylic acid or a group derived from a carboxylic acid, such as acyl, acylalkyl, alkoxycarbonyl, acyloxy, acyloxyalkyl, carboxyalkylamide or alkoxycarbonyloxy.

Examples of heteroalkyl groups are groups of formulae $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, whereby $R^a$ is a hydrogen atom, a $C_1$-$C_6$-alkyl-, a $C_2$-$C_6$-alkenyl- or a $C_2$-$C_6$-alkinyl group; $R^b$ is a hydrogen atom, a $C_1$-$C_6$-alkyl-, a $C_2$-$C_6$-alkenyl- or a $C_2$-$C_6$-alkinyl group; $R^c$ is a hydrogen atom, a $C_1$-$C_6$-alkyl-, a $C_2$-$C_6$-alkenyl- or a $C_2$-$C_6$-alkinyl group; $R^d$ is a hydrogen atom, a $C_1$-$C_6$-alkyl-, a $C_2$-$C_6$-alkenyl- or a $C_2$-$C_6$-alkinyl group and $Y^a$ is a direct bond, a $C_1$-$C_6$-alkylene, a $C_2$-$C_6$-alkenylene or a $C_2$-$C_6$-alkinylene group, whereby each heteroalkyl group contains at least one carbon atom and one or more hydrogen atoms can be replaced by fluorine or chlorine atoms. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, iso-propylethylamino, methyl-aminomethyl, ethylaminomethyl, di-iso-propylaminoethyl, enolether, dimethylaminomethyl, dimethylaminoethyl, acetyl, propionyl, butyryloxy, acetyloxy, methoxycarbonyl, ethoxy-carbonyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (e.g. cycloalkenyl) cyclic group, which has one or more rings (preferably 1 or 2), which contains in particular 3 to 14 ring carbon atoms, preferably 3 to 10 (especially 3, 4, 5, 6 or 7) ring carbon atoms. The expression cycloalkyl further refers to groups in which one or more hydrogen atoms are replaced by fluorine, chlorine, bromine or iodine atoms or —COOH, —OH, =O, —SH, =S, —NH$_2$, =NH or —NO$_2$ groups, that is, for example, cyclic ketones such as cyclohexanone, 2-cyclohexenone or cyclopentanone. Further specific examples of cycloalkyl groups are the cyclopropyl, cyclobutyl, cyclopentyl, spiro[4,5]decanyl, norbornyl, cyclohexyl, cyclopentenyl, cyclohexadienyl, decalinyl, cubanyl, bicyclo[4.3.0]nonyl, tetraline, cyclopentylcyclohexyl, fluorocyclohexyl or the cyclohex-2-enyl group.

The expression heterocycloalkyl refers to a cycloalkyl group as defined above, in which one or more (preferably 1, 2 or 3) ring carbon atoms are replaced by an oxygen, nitrogen, silicon, selenium, phosphorus or sulfur atom (preferably oxygen, sulfur or nitrogen). A heterocycloalkyl group preferably possesses 1 or 2 rings with 3 to 10 (especially 3, 4, 5, 6 or 7) ring atoms. The expression heterocycloalkyl further refers to groups in which one or more hydrogen atoms are replaced by fluorine, chlorine, bromine or iodine atoms or —COOH, —OH, =O, —SH, =S, —NH$_2$, =NH or —NO$_2$ groups. Examples are the piperidyl, morpholinyl, urotropinyl, pyrrolidinyl, tetrahydrothiophenyl, tetrahydropyranyl, tetrahydrofuryl, oxacyclopropyl, azacyclopropyl or 2-pyrazolinyl group, as well as lactams, lactones, cyclic imides and cyclic anhydrides.

The expression alkylcycloalkyl refers to group which, in accordance with the above definitions, contain both cycloalkyl and alkyl, alkenyl or alkinyl groups, e.g. alkylcycloalkyl, alkylcycloalkenyl, alkenylcycloalkyl and alkinylcycloalkyl groups. An alkylcycloalkyl group preferably contains a cycloalkyl group which has one or two rings with 3 to 10 (especially 3, 4, 5, 6 or 7) ring carbon atoms, and one or two alkyl, alkenyl or alkinyl groups with 1 or 2 to 6 carbon atoms.

The expression heteroalkylcycloalkyl refers to alkylcycloalkyl groups as defined above, in which one or more (preferably 1, 2 or 3) ring carbon atoms and/or carbon atoms are replaced by an oxygen, nitrogen, silicon, selenium, phosphorus or sulfur atom (preferably oxygen, sulfur or nitrogen). A heteroalkylcycloalkyl group preferably possesses 1 or 2 rings with 3 to 10 (especially 3, 4, 5, 6 or 7) ring atoms and one or two alkyl, alkenyl, alkinyl or heteroalkyl groups with 1 or 2 to 6 carbon atoms. Examples of such groups are alkylheterocycloalkyl, alkylheterocycloalkenyl, alkenylheterocycloalkyl, alkinylheterocycloalkyl, heteroalkylcycloalkyl, heteroalkylheterocycloalkyl and heteroalkylheterocycloalkenyl, whereby the cyclic groups are saturated or are mono-, di- or tri-unsaturated.

The expression aryl or Ar refers to an aromatic group, which has one or more rings with in particular 6 to 14 ring carbon atoms, preferably 6 to 10 (especially 6) ring carbon atoms. The expression aryl (or Ar) further refers to groups in which one or more hydrogen atoms are replaced by fluorine, chlorine, bromine or iodine atoms or —COOH, —OH, —SH, —NH$_2$, or —NO$_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group which contains one or more rings with in particular 5 to 14 ring atoms, preferably 5 to 10 (especially 5 or 6) ring atoms, and one or more (preferably 1, 2, 3 or 4) oxygen, nitrogen, phosphorus or sulfur ring atoms (preferably O, S or N). The expression heteroaryl further refers to groups in which one or more hydrogen atoms are replaced by fluorine, chlorine, bromine or iodine atoms or —COOH, —OH, —SH, —NH$_2$ or —NO$_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl groups.

The expression aralkyl refers to groups which, in accordance with the above definitions, contain both aryl and alkyl, alkenyl, alkinyl and/or cycloalkyl groups, such as arylalkyl, alkylaryl, arylalkenyl, arylalkinyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic rings with 6 to 10 ring carbon atoms and one or two alkyl, alkenyl and/or alkinyl groups with 1 or 2 to 6 carbon atoms and/or a cycloalkyl group with 5 or 6 ring carbon atoms.

The expression heteroaralkyl refers to an aralkyl group as defined above, in which one or more (preferably 1, 2, 3 or 4) ring carbon atoms and/or carbon atoms are replaced by an oxygen, nitrogen, silicon, selenium, phosphorus, boron or sulfur atom (preferably oxygen, sulfur or nitrogen), i.e. it refers to groups which, in accordance with the above definitions, contain both aryl or heteroaryl, and alkyl, alkenyl, alkinyl and/or heteroalkyl and/or cycloalkyl and/or heterocycloalkyl groups. A heteroaralkyl group preferably contains one or two aromatic rings with 5 or 6 to 10 ring carbon atoms and one or two alkyl, alkenyl and/or alkinyl groups with 1 or 2 to 6 carbon atoms and/or a cycloalkyl group with 5 or 6 ring carbon atoms, whereby 1, 2, 3 or 4 of these carbon atoms are replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkinylheterocycloalkyl, arylalkylheterocycloalkenyl, heteroarylalkyl, heteroarylalkenyl, heteroarylalkinyl, heteroarylheteroalkyl, heteroarylcycloalkyl, heteroarylcycloalkenyl, heteroarylheterocycloalkyl, heteroarylheterocycloalkyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, whereby the cyclic groups are saturated or are monodi- or tri-unsaturated. Specific examples are the tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The expressions cycloalkyl, hereocycloalkyl, alkylcycloalkyl, heteroalkylcycloalkyl, aryl, heteroaryl, aralkyl and heteroaralkyl further refer to groups in which one or more hydrogen atoms are replaced by fluorine, chlorine, bromine or iodine atoms or OH, =O, SH, =S, $NH_2$, =NH or $NO_2$ groups.

The expression "optionally substituted" refers to groups in which one or more hydrogen atoms are replaced e.g. by fluorine, chlorine, bromine or iodine atoms or —COOH, —OH, =O, —SH, =S, —$NH_2$, =NH or —$NO_2$ groups. This expression further refers to groups that are substituted by unsubstituted $C_1$-$C_6$ alkyl, $C_2$-$C_6$ alkenyl, $C_2$-$C_6$ alkinyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Compounds of formula (I) may contain one or more centres of chirality depending on their substitution. The present invention therefore includes both all pure enantiomers and all pure diastereoisomers, and their mixtures in any ratio. In addition, the present invention also includes all cis/trans isomers of the compounds of the general formula (I) as well as mixtures thereof. In addition, the present invention includes all tautomeric forms of the compounds of formula (I).

Preference is given to compounds of formula (I), whereby W is NH and V is O, S or NH, Further preference is given to compounds of formula (I), whereby one, two or three of groups D, G and M are nitrogen atoms.

Particular preference is given to compounds of formula (I), whereby X is a group of formula —$CH_2$—CO—NHOH, —CO—NHOH, —$CH_2$—NOH—CHS, —NOH—CHS, —$CH_2$—NOH—CHO, —NOH—CHO, —$CH_2$—CO—$CH_2$OH, —CO—$CH_2$OH, —$CH_2$—CHOH—CHO, —CHOH—CHO or a group having one of the following formulae:

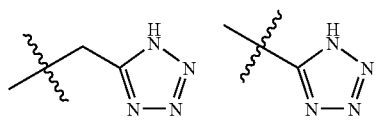

X is most preferably a group of formula —CO—NHOH.

$R_1$ is more preferably a hydrogen atom.

$R_2$ is more preferably a $C_{3-7}$-alkyl- or $C_{3-7}$-heteroalkyl group; especially a n-butyl or n-pentyl group.

$R_3$ is more preferably a hydrogen atom.

$R_4$ is again preferably a hydrogen atom or an optionally substituted heteroaryl radical; especially a hydrogen atom, a pyridyl, benzofuranyl or a p-amino-benzamidinyl radical.

$R_5$ is more preferably a hydrogen atom, an optionally substituted $C_{1-20}$-alkyl group, a branched $C_{1-20}$-alkyl group, an aryl or a heteroaryl group. $R_5$ is particularly preferably an optionally substituted $C_{2-4}$-alkyl group or a branched $C_{2-6}$-alkyl group or a o-, m- or p-substituted or o- and m-disubstituted phenyl group. $R_5$ is particularly preferably a propyl, isopropyl, phenyl, o-nitrophenyl, p-hydroxyphenyl, m-hydroxyphenyl, m,p-dihydroxyphenyl, m-amidinophenyl or 3'-indolyl group.

More preferably, the radicals $R_6$ and $R_7$ are hydrogen atoms.

More preferably, n is 1.

Examples of pharmacologically acceptable salts of compounds of formula (I) are salts of physiologically acceptable mineral acids, such as hydrochloric acid, sulfuric acid and phosphoric acid; or salts of organic acids, such as methanesulfonic acid, p-toluenesulfonic acid, lactic acid, formic acid, acetic acid, trifluoroacetic acid, citric acid, succinic acid, fumaric acid, maleic acid and salicylic acid. Compounds of formula (I) may be solvated, in particular hydrated. Hydration may arise e.g. during the preparation process or as a consequence of the hygroscopic nature of the initially water-free compounds of formula (I).

The pharmaceutical compositions according to the present invention contain at least one compound of formula (I) as active ingredient and optionally carriers and/or adjuvants.

The prodrugs (e.g. R. B. Silverman, Medizinische Chemie, VCH Weinheim, 1995, chapter 8, pp 361ff), which are likewise an object of the present invention, consist of a compound of formula (I) and at least one pharmacologically acceptable protecting group, which is cleaved under physiological conditions, e.g. a hydroxy, alkoxy, aralkyloxy, acyl or acyloxy group, such as a methoxy, ethoxy, benzyloxy, acetyl or acetyloxy group.

The therapeutical usage of the compounds of formula (I), their pharmacologically acceptable salts or solvates and hydrates, as well as formulations and pharmaceutical compositions, is likewise an object of the present invention.

Compounds of formula (I) are of great interest, according to the invention, especially as inhibitors of metalloproteinases (in particular PDF). The usage of these active ingredients in the production of medicaments to prevent and/or treat diseases, especially those conveyed by PDF, is also an object of the present invention. In general, compounds of formula (I) are administered using known, acceptable methods, either singly or in combination with any other therapeutic agent. Administration may be effected e.g. in one of the following ways: orally, e.g. as dragées, coated tablets, pills, semi-solids, soft or hard capsules, solutions, emulsions or suspensions; parenterally, e.g. as an injectable solution; rectally as suppositories; by inhalation, e.g. as a powder formulation or spray, transdermally or intra-nasally. To produce such tablets, pills, semi-solids, coated tablets, dragées and hard gelatin capsules, the therapeutically employable product may be mixed with pharmacologically inert, inorganic or organic carriers for medicaments, e.g. with lactose, sucrose, glucose, gelatin, malt, silica gel, starch or derivatives thereof, talc, stearic acid or salts thereof, dry skimmed milk and the like. To produce soft capsules, carriers for medicaments, such as vegetable oils, petroleum, animal or synthetic oils, wax, fat, polyols, may be used. To produce liquid solutions and syrups, carriers for medicaments, such as water, alcohols, aqueous salt solution, aqueous dextrose, polyols, glycerol, vegetable oils, petroleum, animal or synthetic oils, may be used. For suppositories, carriers for medicaments, such as vegetable oils, petroleum, animal or synthetic oils, wax, fat and polyols, may be used. For aerosol formulations, compressed gases that are appropriate for this purpose may be used, such as oxygen, nitrogen and carbon dioxide. The pharmaceutically acceptable agents may also contain preserving and stabilizing additives, emulsifiers, sweeteners, aromatics, salts to modify the osmotic pressure, buffers, coating additives and antioxidants.

Compounds of formula (I) may be produced by reacting compounds of formulae X—[$CR_1R_2$]$_n$—$NH_2$ (II), $R_3$—CO—$R_4$ (III) and $R_5$—CH$_2$—CO—COOEt (IV), whereby the radicals are defined as above.

EXAMPLES

General Procedure:

50 µl of a 0.2 M solution of amine (II) in ethanol:dichloromethane (1:1) were dispensed onto a 96-well plate. 50 µl of a 0.2 M solution of the aldehyde ($R^3$=H) or ketone (III) in ethanol:dichloromethane (1:1) were added. The plate was shaken for 20 mins at room temperature. Subsequently, 50 µl of a 0.2 M solution of the keto acid (IV) in ethanol:dichloromethane (1:1) were dispensed. The plate was shaken over night at room temperature and the solvent subsequently evaporated.

The following compounds were produced in accordance with the general procedure, using appropriate starting materials, and were identified by mass spectrometry. All compounds were investigated for their activity as PDF inhibitors (for the assay, see D. Chen et al. Antimicrobial Agents and Chemotherapy, January 2004, pp. 250-261) and had IC$_{50}$ values ranging between 1 nmol and 50 µmol.

|  | calc. [M + H] | found [M + H] | calc. [M + Na] | found [M + Na] |
|---|---|---|---|---|
| 2-(4-ethyl-3-hydroxy-2-oxo-2,5-dihydro-pyrrol-1-yl)-hexanoic acid hydroxyamide | 257.18 | n.d. | 279.17 | 279.14 |
| 2-(2-benzofuran-2-yl-4-hydroxy-3-isopropyl-5-oxo-2,5-dihydro-pyrrol-1-yl)-hexanoic acid hydroxyamide | 387.23 | n.d. | 409.22 | 409.24 |
| 2-[3-hydroxy-4-methyl-2-oxo-5-(1-oxo-1,2,3,4-tetrahydro-naphthalen-2-yl)-2,5-dihydro-pyrrol-1-yl]-hexanoic acid hydroxyamide | 387.23 | 387.26 | 409.22 | 409.3 |
| 2-(2-benzofuran-2-yl-4-hydroxy-3-methyl-5-oxo-2,5-dihydro-pyrrol-1-yl)-hexanoic acid hydroxyamide | 359.2 | 359.23 | 381.18 | 381.14 |
| 2-[3-hydroxy-4-methyl-2-oxo-5-(2-oxo-cyclohexyl)-2,5-dihydro-pyrrol-1-yl]-hexanoic acid hydroxyamide | 339.24 | 339.25 | 361.22 | 361.25 |
| 2-(3-hydroxy-4-methyl-2-oxo-2,5-dihydro-pyrrol-1-yl)-hexanoic acid hydroxyamide | 243.16 | 243.18 | 265.15 | 265.19 |
| 3-(2-cyclopropyl-4-hydroxy-3-methylsulfanylmethyl-5-oxo-2,5-dihydro-pyrrol-1-yl)-N-hydroxy-propionamide | 287.14 | 287.17 | 309.12 | n.d. |
| N-hydroxy-2-(3-hydroxy-5-methyl-2-oxo-4-phenyl-2,5-dihydro-pyrrol-1-yl)-acetamide | 263.12 | 263.17 | 285.11 | 285.13 |
| 2-(3-ethyl-4-hydroxy-5-oxo-2-quinolin-2-yl-2,5-dihydro-pyrrol-1-yl)-hexanoic acid hydroxyamide | 384.23 | 384.22 | 406.21 | n.d. |
| 2-[3-hydroxy-4-isopropyl-5-(1-methyl-1H-imidazol-2-yl)-2-oxo-2,5-dihydro-pyrrol-1-yl]-hexanoic acid hydroxyamide | 351.25 | 351.24 | 373.23 | n.d. |
| 2-(2-benzofuran-2-yl-4-hydroxy-5-oxo-3-propyl-2,5-dihydro-pyrrol-1-yl)-hexanoic acid hydroxyamide | 387.23 | 387.22 | 409.22 | 409.21 |
| 2-(3-hydroxy-4-isopropyl-2-oxo-2,5-dihydro-pyrrol-1-yl)-hexanoic acid hydroxyamide | 271.2 | 271.21 | 293.19 | 293.16 |
| 2-[3-hydroxy-5-(5-methyl-3H-imidazol-4-yl)-2-oxo-4-propyl-2,5-dihydro-pyrrol-1-yl]-hexanoic acid hydroxyamide | 351.25 | 351.24 | 373.23 | n.d. |
| 2-(3-ethyl-4-hydroxy-5-oxo-2-quinolin-4-yl-2,5-dihydro-pyrrol-1-yl)-hexanoic acid hydroxyamide | 384.23 | 384.24 | 406.21 | n.d. |
| 2-[3-ethyl-4-hydroxy-5-oxo-2-(2-phenyl-propyl)-2,5-dihydro-pyrrol-1-yl]-hexanoic acid hydroxyamide | 375.28 | 375.26 | 397.26 | 397.24 |
| 2-(3-hydroxy-2-oxo-4-phenyl-2,5-dihydro-pyrrol-1-yl)-hexanoic acid hydroxyamide | 305.18 | 305.19 | 327.16 | 327.17 |
| 2-[2-(4-carbamimidoyl-phenyl)-4-hydroxy-3-methyl-5-oxo-2,5-dihydro-pyrrol-1-yl]-hexanoic acid hydroxyamide | 361.23 | n.d. | 383.21 | 383.27 |
| 2-(3-ethyl-4-hydroxy-5-oxo-2-quinolin-3-yl-2,5-dihydro-pyrrol-1-yl)-hexanoic acid hydroxyamide | 384.23 | 384.23 | 406.21 | n.d. |
| 2-(3-hydroxy-4-isopropyl-5-methyl-2-oxo-2,5-dihydro-pyrrol-1-yl)-hexanoic acid hydroxyamide | 285.22 | 285.21 | 307.21 | 307.27 |
| 2-{3-hydroxy-5-[2-(5-methyl-furan-2-yl)-propyl]-2-oxo-4-propyl-2,5-dihydro-pyrrol-1-yl}-hexanoic acid hydroxyamide | 393.29 | 393.27 | 415.28 | 415.28 |
| 2-(3-hydroxy-4-methyl-2-oxo-5-quinolin-4-yl-2,5-dihydro-pyrrol-1-yl)-hexanoic acid hydroxyamide | 370.21 | 370.22 | 392.19 | n.d. |
| 2-(3-hydroxy-4-methyl-2-oxo-5-propyl-2,5-dihydro-pyrrol-1-yl)-hexanoic acid hydroxyamide | 285.22 | 285.23 | 307.21 | n.d. |
| 2-[3-ethyl-4-hydroxy-2-(6-methyl-pyridin-2-yl)-5-oxo-2,5-dihydro-pyrrol-1-yl]-hexanoic acid hydroxyamide | 348.23 | 348.23 | 370.22 | 370.2 |
| 2-[3-hydroxy-4-methyl-2-oxo-5-(4-pyridin-2-yl-phenyl)-2,5-dihydro-pyrrol-1-yl]-hexanoic acid hydroxyamide | 396.23 | 396.26 | 418.21 | n.d. |
| 2-[3-ethyl-4-hydroxy-2-(2-methylsulfanyl-ethyl)-5-oxo-2,5-dihydro-pyrrol-1-yl]-hexanoic acid hydroxyamide | 331.21 | 331.2 | 353.2 | 353.22 |

-continued

| | calc. [M + H] | found [M + H] | calc. [M + Na] | found [M + Na] |
|---|---|---|---|---|
| 2-(3-ethyl-4-hydroxy-5-oxo-2-quinolin-8-yl-2,5-dihydro-pyrrol-1-yl)-hexanoic acid hydroxyamide | 384.23 | 384.24 | 406.21 | n.d. |
| 2-(3-hydroxy-4-methyl-2-oxo-5-quinolin-3-yl-2,5-dihydro-pyrrol-1-yl)-hexanoic acid hydroxyamide | 370.21 | 370.22 | 392.19 | n.d. |
| 2-[3-hydroxy-4-(3-hydroxy-phenyl)-2-oxo-2,5-dihydro-pyrrol-1-yl]-hexanoic acid hydroxyamide | 321.18 | 321.17 | 343.16 | 343.17 |
| 2-(3-hydroxy-2-oxo-4-propyl-5-quinolin-2-yl-2,5-dihydro-pyrrol-1-yl)-hexanoic acid hydroxyamide | 398.25 | 398.26 | 420.23 | 420.24 |
| 2-(3-hydroxy-2-oxo-4-propyl-5-pyridin-2-yl-2,5-dihydro-pyrrol-1-yl)-hexanoic acid hydroxyamide | 348.23 | 348.22 | 370.22 | 370.21 |
| 2-{3-ethyl-2-[2-(4-fluoro-phenyl)-2-oxo-ethyl]-4-hydroxy-5-oxo-2,5-dihydro-pyrrol-1-yl}-hexanoic acid hydroxyamide | 393.22 | 393.24 | 415.2 | 415.2 |
| 2-(3-hydroxy-2-oxo-4-propyl-5-pyridin-4-yl-2,5-dihydro-pyrrol-1-yl)-hexanoic acid hydroxyamide | 348.23 | 348.23 | 370.22 | n.d. |
| 2-(3-ethyl-4-hydroxy-5-oxo-2-pyridin-3-yl-2,5-dihydro-pyrrol-1-yl)-hexanoic acid hydroxyamide | 334.21 | 334.21 | 356.2 | n.d. |
| 2-(3-hydroxy-5-isopropyl-4-methyl-2-oxo-2,5-dihydro-pyrrol-1-yl)-hexanoic acid hydroxyamide | 285.22 | 285.21 | 307.21 | 307.2 |
| 2-(2,3-diethyl-4-hydroxy-5-oxo-2,5-dihydro-pyrrol-1-yl)-hexanoic acid hydroxyamide | 285.22 | 285.2 | 307.21 | n.d. |
| 2-[3-hydroxy-5-(1H-imidazol-2-yl)-2-oxo-4-phenyl-2,5-dihydro-pyrrol-1-yl]-hexanoic acid hydroxyamide | 371.21 | 371.21 | 393.19 | n.d. |
| 2-{3-ethyl-4-hydroxy-2-[2-(5-methyl-furan-2-yl)-propyl]-5-oxo-2,5-dihydro-pyrrol-1-yl}-hexanoic acid hydroxyamide | 379.27 | 379.28 | 401.26 | 401.18 |
| 2-(2-ethyl-4-hydroxy-3-isopropyl-5-oxo-2,5-dihydro-pyrrol-1-yl)-hexanoic acid hydroxyamide | 299.24 | 299.24 | 321.22 | 321.21 |
| 2-[3-ethyl-4-hydroxy-2-(5-methyl-3H-imidazol-4-yl)-5-oxo-2,5-dihydro-pyrrol-1-yl]-hexanoic acid hydroxyamide | 337.23 | 337.31 | 359.21 | n.d. |
| 2-(3-ethyl-4-hydroxy-5-oxo-2-phenethyl-2,5-dihydro-pyrrol-1-yl)-hexanoic acid hydroxyamide | 361.26 | 361.26 | 383.24 | 383.22 |
| 2-[3-hydroxy-4-isopropyl-5-(5-methyl-3H-imidazol-4-yl)-2-oxo-2,5-dihydro-pyrrol-1-yl]-hexanoic acid hydroxyamide | 351.25 | 351.26 | 373.23 | n.d. |
| 2-(3-hydroxy-4-isopropyl-2-oxo-5-quinolin-2-yl-2,5-dihydro-pyrrol-1-yl)-hexanoic acid hydroxyamide | 398.25 | 398.27 | 420.23 | n.d. |
| 2-[3-hydroxy-5-(1-methyl-1H-imidazol-2-yl)-2-oxo-4-phenyl-2,5-dihydro-pyrrol-1-yl]-hexanoic acid hydroxyamide | 385.23 | 385.23 | 407.21 | n.d. |
| 2-(3-hydroxy-4-methyl-2-oxo-5-quinolin-2-yl-2,5-dihydro-pyrrol-1-yl)-hexanoic acid hydroxyamide | 370.21 | 370.21 | 392.19 | n.d. |
| 2-[3-hydroxy-4-methyl-2-oxo-5-(tetrahydro-furan-3-yl)-2,5-dihydro-pyrrol-1-yl]-hexanoic acid hydroxyamide | 313.22 | 313.21 | 335.2 | 335.19 |
| 2-(2-butyl-4-hydroxy-3-methyl-5-oxo-2,5-dihydro-pyrrol-1-yl)-hexanoic acid hydroxyamide | 299.24 | 299.19 | 321.22 | 321.22 |
| 2-{3-hydroxy-4-isopropyl-5-[2-(5-methyl-furan-2-yl)-propyl]-2-oxo-2,5-dihydro-pyrrol-1-yl}-hexanoic acid hydroxyamide | 393.29 | 393.27 | 415.28 | 415.28 |
| 2-(3-ethyl-4-hydroxy-2-isobutyl-5-oxo-2,5-dihydro-pyrrol-1-yl)-hexanoic acid hydroxyamide | 313.26 | 313.18 | 335.24 | 335.25 |
| 2-(3-hydroxy-4-methyl-2-oxo-5-pyridin-2-yl-2,5-dihydro-pyrrol-1-yl)-hexanoic acid hydroxyamide | 320.19 | n.d. | 342.18 | 342.18 |
| 2-(3-hydroxy-4-isopropyl-2-oxo-5-pyridin-2-yl-2,5-dihydro-pyrrol-1-yl)-hexanoic acid hydroxyamide | 348.23 | 348.24 | 370.22 | 370.21 |
| 2-[3-hydroxy-4-(4-hydroxy-phenyl)-2-oxo-2,5-dihydro-pyrrol-1-yl]-hexanoic acid hydroxyamide | 321.18 | 321.18 | 343.16 | 343.16 |
| 2-(3-hydroxy-5-methyl-2-oxo-4-phenyl-2,5-dihydro-pyrrol-1-yl)-hexanoic acid hydroxyamide | 319.2 | n.d. | 341.18 | 341.17 |
| 2-[3-hydroxy-5-(1-methyl-1H-imidazol-2-yl)-4-methylsulfanylmethyl-2-oxo-2,5-dihydro-pyrrol-1-yl]-hexanoic acid hydroxyamide | 369.2 | 369.14 | 391.18 | n.d. |
| 2-{2-[(E)-2-(4-dimethylamino-phenyl)-vinyl]-4-hydroxy-3-isopropyl-5-oxo-2,5-dihydro-pyrrol-1-yl}-hexanoic acid hydroxyamide | 416.31 | 416.28 | 438.29 | n.d. |
| 2-(3-hydroxy-4-isopropyl-2-oxo-5-pyridin-4-yl-2,5-dihydro-pyrrol-1-yl)-hexanoic acid hydroxyamide | 348.23 | 348.24 | 370.22 | n.d. |
| 2-(3-hydroxy-4-methyl-2-oxo-5-thiazol-2-yl-2,5-dihydro-pyrrol-1-yl)-hexanoic acid hydroxyamide | 326.15 | 326.15 | 348.13 | n.d. |
| 2-[3-hydroxy-4-methyl-2-oxo-5-(2-phenyl-propyl)-2,5-dihydro-pyrrol-1-yl]-hexanoic acid hydroxyamide | 361.26 | 361.24 | 383.24 | 383.25 |

| | calc. [M + H] | found [M + H] | calc. [M + Na] | found [M + Na] |
|---|---|---|---|---|
| 2-[3-hydroxy-4-isopropyl-5-(5-methyl-2,4-dioxo-3,4-dihydro-2H-pyrimidin-1-ylmethyl)-2-oxo-2,5-dihydro-pyrrol-1-yl]-hexanoic acid hydroxyamide | 409.25 | 409.26 | 431.24 | 431.23 |
| 2-(3-hydroxy-4-methyl-2-oxo-5-thiophen-2-yl-2,5-dihydro-pyrrol-1-yl)-hexanoic acid hydroxyamide | 325.15 | 325.19 | 347.14 | n.d. |
| 2-[3-hydroxy-4-(1H-indol-3-yl)-2-oxo-2,5-dihydro-pyrrol-1-yl]-hexanoic acid hydroxyamide | 344.19 | 344.2 | 366.18 | 366.17 |
| 2-[3-ethyl-4-hydroxy-5-oxo-2-(2-oxo-cyclohexyl)-2,5-dihydro-pyrrol-1-yl]-hexanoic acid hydroxyamide | 353.26 | 353.26 | 375.24 | n.d. |
| 2-[3-hydroxy-4-methyl-5-(6-methyl-pyridin-2-yl)-2-oxo-2,5-dihydro-pyrrol-1-yl]-hexanoic acid hydroxyamide | 334.21 | 334.22 | 356.2 | n.d. |
| 2-[3-hydroxy-5-(5-methyl-3H-imidazol-4-yl)-2-oxo-4-phenyl-2,5-dihydro-pyrrol-1-yl]-hexanoic acid hydroxyamide | 385.23 | 385.23 | 407.21 | n.d. |
| 2-(2-benzyloxymethyl-4-hydroxy-3-isopropyl-5-oxo-2,5-dihydro-pyrrol-1-yl)-hexanoic acid hydroxyamide | 391.27 | 391.28 | 413.26 | 413.26 |
| 2-(3-hydroxy-4-methyl-2-oxo-5-pentyl-2,5-dihydro-pyrrol-1-yl)-hexanoic acid hydroxyamide | 313.26 | 313.26 | 335.24 | n.d. |
| 2-[2-(4,5-dimethyl-furan-2-yl)-4-hydroxy-3-isopropyl-5-oxo-2,5-dihydro-pyrrol-1-yl]-hexanoic acid hydroxyamide | 365.26 | 365.27 | 387.24 | n.d. |
| 2-(2-ethyl-4-hydroxy-5-oxo-3-propyl-2,5-dihydro-pyrrol-1-yl)-hexanoic acid hydroxyamide | 299.24 | 299.22 | 321.22 | 321.2 |
| 2-(3-hydroxy-4-isopropyl-2-oxo-5-propyl-2,5-dihydro-pyrrol-1-yl)-hexanoic acid hydroxyamide | 313.26 | 313.22 | 335.24 | 335.23 |
| 2-(3-hydroxy-4-isopropyl-2-oxo-5-phenethyl-2,5-dihydro-pyrrol-1-yl)-hexanoic acid hydroxyamide | 375.28 | 375.27 | 397.26 | 397.26 |
| 2-(3-hydroxy-4-isopropyl-2-oxo-5-thiazol-2-yl-2,5-dihydro-pyrrol-1-yl)-hexanoic acid hydroxyamide | 354.19 | 354.15 | 376.17 | 376.19 |
| 2-[3-ethyl-4-hydroxy-5-oxo-2-(1-oxo-1,2,3,4-tetrahydro-naphthalen-2-yl)-2,5-dihydro-pyrrol-1-yl]-hexanoic acid hydroxyamide | 401.25 | 401.26 | 423.24 | 423.27 |
| 2-[3-hydroxy-4-methyl-5-(1-methyl-butyl)-2-oxo-2,5-dihydro-pyrrol-1-yl]-hexanoic acid hydroxyamide | 313.26 | 313.21 | 335.24 | 335.27 |
| 2-[3-hydroxy-5-(1-methyl-1H-imidazol-2-yl)-2-oxo-4-pentyl-2,5-dihydro-pyrrol-1-yl]-hexanoic acid hydroxyamide | 379.29 | 379.28 | 401.27 | n.d. |
| 2-(3-ethyl-4-hydroxy-5-oxo-2-propyl-2,5-dihydro-pyrrol-1-yl)-hexanoic acid hydroxyamide | 299.24 | n.d. | 321.22 | 321.19 |
| 2-(3-ethyl-4-hydroxy-5-oxo-2-pyridin-2-yl-2,5-dihydro-pyrrol-1-yl)-hexanoic acid hydroxyamide | 334.21 | 334.18 | 356.2 | 356.2 |
| 2-[3-hydroxy-4-isopropyl-5-(4-nitro-phenyl)-2-oxo-2,5-dihydro-pyrrol-1-yl]-hexanoic acid hydroxyamide | 392.22 | 392.23 | 414.2 | n.d. |
| 2-[3-ethyl-4-hydroxy-5-oxo-2-(tetrahydro-furan-3-yl)-2,5-dihydro-pyrrol-1-yl]-hexanoic acid hydroxyamide | 327.24 | 327.2 | 349.22 | 349.22 |
| 2-(3-ethyl-4-hydroxy-2-isopropyl-5-oxo-2,5-dihydro-pyrrol-1-yl)-hexanoic acid hydroxyamide | 299.24 | 299.21 | 321.22 | 321.24 |
| 2-[3-ethyl-2-(3-fluoro-phenyl)-4-hydroxy-5-oxo-2,5-dihydro-pyrrol-1-yl]-hexanoic acid hydroxyamide | 351.21 | 351.21 | 373.19 | 373.23 |
| 2-[3-ethyl-4-hydroxy-5-oxo-2-(4-trifluoromethyl-phenyl)-2,5-dihydro-pyrrol-1-yl]-hexanoic acid hydroxyamide | 401.2 | 401.23 | 423.19 | 423.21 |
| 2-(3-ethyl-4-hydroxy-5-oxo-2-pyridin-4-yl-2,5-dihydro-pyrrol-1-yl)-hexanoic acid hydroxyamide | 334.21 | 334.22 | 356.2 | n.d. |
| 2-[2-(3-bromo-phenyl)-4-hydroxy-5-oxo-3-propyl-2,5-dihydro-pyrrol-1-yl]-hexanoic acid hydroxyamide | 425.15 | 425.17 | 447.13 | n.d. |
| 2-(3-hydroxy-4-methyl-2-oxo-5-phenethyl-2,5-dihydro-pyrrol-1-yl)-hexanoic acid hydroxyamide | 347.24 | 347.24 | 369.22 | 369.24 |
| 2-(3-hydroxy-2-oxo-4-propyl-5-thiazol-2-yl-2,5-dihydro-pyrrol-1-yl)-hexanoic acid hydroxyamide | 354.19 | 354.2 | 376.17 | 376.14 |
| 2-[3-hydroxy-5-(1H-imidazol-2-yl)-4-methyl-2-oxo-2,5-dihydro-pyrrol-1-yl]-hexanoic acid hydroxyamide | 309.19 | 309.16 | 331.17 | n.d. |
| 2-[4-(3,4-dihydroxy-phenyl)-3-hydroxy-2-oxo-2,5-dihydro-pyrrol-1-yl]-hexanoic acid hydroxyamide | 337.17 | 337.19 | 359.15 | 359.15 |
| 2-(3-hydroxy-2-oxo-4-propyl-5-quinolin-3-yl-2,5-dihydro-pyrrol-1-yl)-hexanoic acid hydroxyamide | 398.25 | 398.27 | 420.23 | n.d. |
| 2-[2-(4-cyano-phenyl)-4-hydroxy-3-isopropyl-5-oxo-2,5-dihydro-pyrrol-1-yl]-hexanoic acid hydroxyamide | 372.23 | 372.24 | 394.21 | 394.21 |

|  | calc. [M + H] | found [M + H] | calc. [M + Na] | found [M + Na] |
|---|---|---|---|---|
| 2-[3-hydroxy-4-isopropyl-5-(6-methyl-pyridin-2-yl)-2-oxo-2,5-dihydro-pyrrol-1-yl]-hexanoic acid hydroxyamide | 362.25 | 362.25 | 384.24 | 384.25 |
| 2-[3-hydroxy-4-isopropyl-2-oxo-5-(4-trifluoromethyl-phenyl)-2,5-dihydro-pyrrol-1-yl]-hexanoic acid hydroxyamide | 415.22 | 415.24 | 437.21 | 437.21 |
| 2-(2-benzyl-4-hydroxy-3-methylsulfanylmethyl-5-oxo-2,5-dihydro-pyrrol-1-yl)-hexanoic acid hydroxyamide | 379.21 | 379.22 | 401.19 | 401.18 |
| 2-[3-hydroxy-4-isopropyl-2-oxo-5-(2-phenyl-propyl)-2,5-dihydro-pyrrol-1-yl]-hexanoic acid hydroxyamide | 389.3 | 389.28 | 411.28 | 411.28 |
| 2-(3-hydroxy-5-isopropyl-2-oxo-4-phenyl-2,5-dihydro-pyrrol-1-yl)-hexanoic acid hydroxyamide | 347.24 | 347.27 | 369.22 | 369.24 |
| 2-[3-hydroxy-5-(1H-imidazol-2-yl)-4-(1H-indol-3-yl)-2-oxo-2,5-dihydro-pyrrol-1-yl]-hexanoic acid hydroxyamide | 410.22 | 410.23 | 432.2 | n.d. |
| 2-[3-hydroxy-4-isopropyl-5-(5-methyl-thiophen-2-yl)-2-oxo-2,5-dihydro-pyrrol-1-yl]-hexanoic acid hydroxyamide | 367.21 | n.d. | 389.19 | 389.18 |
| 2-[3-hydroxy-5-(5-methyl-3H-imidazol-4-yl)-2-oxo-4-pentyl-2,5-dihydro-pyrrol-1-yl]-hexanoic acid hydroxyamide | 379.29 | 379.29 | 401.27 | n.d. |
| 2-[3-hydroxy-4-methyl-5-(5-methyl-3H-imidazol-4-yl)-2-oxo-2,5-dihydro-pyrrol-1-yl]-hexanoic acid hydroxyamide | 323.21 | 323.21 | 345.19 | n.d. |
| 2-(3-hydroxy-5-isopropyl-4-methylsulfanylmethyl-2-oxo-2,5-dihydro-pyrrol-1-yl)-hexanoic acid hydroxyamide | 331.21 | 331.16 | 353.2 | 353.19 |
| 2-[3-hydroxy-4-(1H-indol-3-yl)-5-methyl-2-oxo-2,5-dihydro-pyrrol-1-yl]-hexanoic acid hydroxyamide | 358.21 | 358.23 | 380.2 | 380.21 |
| 2-(3-ethyl-4-hydroxy-5-oxo-2-thiazol-2-yl-2,5-dihydro-pyrrol-1-yl)-hexanoic acid hydroxyamide | 340.17 | 340.19 | 362.15 | 362.16 |
| 2-(3-hydroxy-4-isopropyl-2-oxo-5-quinolin-4-yl-2,5-dihydro-pyrrol-1-yl)-hexanoic acid hydroxyamide | 398.25 | 398.26 | 420.23 | n.d. |
| 2-[3-ethyl-4-hydroxy-5-oxo-2-(1-phenyl-ethyl)-2,5-dihydro-pyrrol-1-yl]-hexanoic acid hydroxyamide | 361.26 | 361.27 | 383.24 | 383.25 |
| 2-[3-hydroxy-5-(1-methyl-butyl)-2-oxo-4-propyl-2,5-dihydro-pyrrol-1-yl]-hexanoic acid hydroxyamide | 341.3 | 341.27 | 363.28 | 363.26 |
| 2-[3-hydroxy-5-(3-hydroxy-phenyl)-4-isopropyl-2-oxo-2,5-dihydro-pyrrol-1-yl]-hexanoic acid hydroxyamide | 363.24 | 363.24 | 385.22 | 385.24 |
| 2-[3-fluoro-4-hydroxy-5-oxo-2-((E)-pent-1-enyl)-2,5-dihydro-pyrrol-1-yl]-hexanoic acid hydroxyamide | 315.21 | n.d. | 337.19 | 337.16 |
| 2-[3-hydroxy-5-(4-hydroxy-phenyl)-2-oxo-4-propyl-2,5-dihydro-pyrrol-1-yl]-hexanoic acid hydroxyamide | 363.24 | 363.29 | 385.22 | n.d. |
| 2-[3-ethyl-4-hydroxy-5-oxo-2-(4-pyridin-2-yl-phenyl)-2,5-dihydro-pyrrol-1-yl]-hexanoic acid hydroxyamide | 410.25 | 410.26 | 432.23 | n.d. |
| 2-[3-hydroxy-5-(6-methyl-pyridin-2-yl)-2-oxo-4-phenyl-2,5-dihydro-pyrrol-1-yl]-hexanoic acid hydroxyamide | 396.23 | 396.24 | 418.21 | n.d. |
| 2-[2-(1,5-dimethyl-hex-4-enyl)-3-ethyl-4-hydroxy-5-oxo-2,5-dihydro-pyrrol-1-yl]-hexanoic acid hydroxyamide | 367.32 | 367.31 | 389.3 | 389.3 |
| 2-[2-(3-chloro-phenyl)-4-hydroxy-3-isopropyl-5-oxo-2,5-dihydro-pyrrol-1-yl]-hexanoic acid hydroxyamide | 381.2 | 381.2 | 403.18 | 403.2 |
| 2-(3-hydroxy-4-isopropyl-2-oxo-5-thiophen-3-yl-2,5-dihydro-pyrrol-1-yl)-hexanoic acid hydroxyamide | 353.19 | 353.19 | 375.18 | 375.18 |
| 2-{2-[(E)-2-(4-dimethylamino-phenyl)-vinyl]-3-ethyl-4-hydroxy-5-oxo-2,5-dihydro-pyrrol-1-yl}-hexanoic acid hydroxyamide | 402.29 | 402.3 | 424.27 | n.d. |
| 2-[2-ethyl-4-hydroxy-3-(3-hydroxy-phenyl)-5-oxo-2,5-dihydro-pyrrol-1-yl]-hexanoic acid hydroxyamide | 349.22 | 349.22 | 371.2 | 371.22 |
| 2-(3-hydroxy-4,5-diisopropyl-2-oxo-2,5-dihydro-pyrrol-1-yl)-hexanoic acid hydroxyamide | 313.26 | 313.33 | 335.24 | 335.24 |
| 2-(3-hydroxy-4-methylsulfanylmethyl-2-oxo-5-pyridin-2-yl-2,5-dihydro-pyrrol-1-yl)-hexanoic acid hydroxyamide | 366.19 | 366.2 | 388.17 | n.d. |
| 2-{2-[2-(4-fluoro-phenyl)-2-oxo-ethyl]-4-hydroxy-3-methyl-5-oxo-2,5-dihydro-pyrrol-1-yl}-hexanoic acid hydroxyamide | 379.2 | 379.21 | 401.19 | 401.21 |

| | calc. [M + H] | found [M + H] | calc. [M + Na] | found [M + Na] |
|---|---|---|---|---|
| 2-(3-hydroxy-4-methylsulfanylmethyl-2-oxo-5-pyridin-4-yl-2,5-dihydro-pyrrol-1-yl)-hexanoic acid hydroxyamide | 366.19 | 366.21 | 388.17 | n.d. |
| 2-[3-hydroxy-2-oxo-4-propyl-5-(4-trifluoromethyl-phenyl)-2,5-dihydro-pyrrol-1-yl]-hexanoic acid hydroxyamide | 415.22 | 415.25 | 437.21 | 437.24 |
| 2-[2-(2-benzo[1,3]dioxol-5-yl-1-methyl-ethyl)-4-hydroxy-3-isopropyl-5-oxo-2,5-dihydro-pyrrol-1-yl]-hexanoic acid hydroxyamide | 433.29 | 433.29 | 455.27 | 455.26 |
| 2-[2-(1,5-dimethyl-hex-4-enyl)-4-hydroxy-3-methyl-5-oxo-2,5-dihydro-pyrrol-1-yl]-hexanoic acid hydroxyamide | 353.3 | 353.29 | 375.28 | 375.29 |
| 2-[2-(2-chloro-phenyl)-4-hydroxy-3-methyl-5-oxo-2,5-dihydro-pyrrol-1-yl]-hexanoic acid hydroxyamide | 353.16 | n.d. | 375.14 | 375.14 |
| 2-[3-hydroxy-4-methyl-2-oxo-5-(4-trifluoromethyl-phenyl)-2,5-dihydro-pyrrol-1-yl]-hexanoic acid hydroxyamide | 387.19 | 387.22 | 409.17 | 409.2 |
| 2-(2-furan-2-yl-4-hydroxy-3-isopropyl-5-oxo-2,5-dihydro-pyrrol-1-yl)-hexanoic acid hydroxyamide | 337.22 | 337.21 | 359.2 | 359.15 |
| 2-[2-(3,4-difluoro-phenyl)-4-hydroxy-3-methyl-5-oxo-2,5-dihydro-pyrrol-1-yl]-hexanoic acid hydroxyamide | 355.18 | 355.19 | 377.16 | 377.18 |
| 2-(2-benzyl-4-hydroxy-3-isopropyl-5-oxo-2,5-dihydro-pyrrol-1-yl)-hexanoic acid hydroxyamide | 361.26 | 361.27 | 383.24 | 383.26 |
| 2-[2-(2,3-difluoro-phenyl)-3-ethyl-4-hydroxy-5-oxo-2,5-dihydro-pyrrol-1-yl]-hexanoic acid hydroxyamide | 369.2 | 369.21 | 391.18 | 391.18 |
| 2-[2-(4-chloro-3-trifluoromethyl-phenyl)-4-hydroxy-3-isopropyl-5-oxo-2,5-dihydro-pyrrol-1-yl]-hexanoic acid hydroxyamide | 449.18 | 449.21 | 471.16 | n.d. |
| 2-(3-hydroxy-2-oxo-4-phenyl-5-pyridin-4-yl-2,5-dihydro-pyrrol-1-yl)-hexanoic acid hydroxyamide | 382.21 | 382.22 | 404.19 | n.d. |
| 2-[3-ethyl-2-(4-fluoro-phenyl)-4-hydroxy-5-oxo-2,5-dihydro-pyrrol-1-yl]-hexanoic acid hydroxyamide | 351.21 | 351.22 | 373.19 | 373.21 |
| 2-(3-hydroxy-4-isopropyl-2-oxo-5-thiophen-2-yl-2,5-dihydro-pyrrol-1-yl)-hexanoic acid hydroxyamide | 353.19 | 353.21 | 375.18 | 375.19 |
| 2-[2-(4-chloro-phenyl)-4-hydroxy-3-methyl-5-oxo-2,5-dihydro-pyrrol-1-yl]-hexanoic acid hydroxyamide | 353.16 | 353.17 | 375.14 | 375.14 |
| 2-[3-hydroxy-5-(5-methyl-furan-2-yl)-2-oxo-4-propyl-2,5-dihydro-pyrrol-1-yl]-hexanoic acid hydroxyamide | 351.24 | 351.27 | 373.22 | n.d. |
| 2-(3-hydroxy-2-oxo-4-pentyl-5-pyridin-2-yl-2,5-dihydro-pyrrol-1-yl)-hexanoic acid hydroxyamide | 376.27 | 376.27 | 398.25 | n.d. |
| 2-(3-hydroxy-4-methyl-2-oxo-5-m-tolyl-2,5-dihydro-pyrrol-1-yl)-hexanoic acid hydroxyamide | 333.22 | 333.22 | 355.2 | 355.2 |
| 2-[2-(2,3-dichloro-phenyl)-4-hydroxy-5-oxo-3-propyl-2,5-dihydro-pyrrol-1-yl]-hexanoic acid hydroxyamide | 415.16 | 415.17 | 437.14 | 437.16 |
| 2-(2-benzyloxymethyl-4-hydroxy-3-methyl-5-oxo-2,5-dihydro-pyrrol-1-yl)-hexanoic acid hydroxyamide | 363.24 | 363.24 | 385.22 | 385.16 |
| 2-[3-hydroxy-5-(4-nitro-phenyl)-2-oxo-4-propyl-2,5-dihydro-pyrrol-1-yl]-hexanoic acid hydroxyamide | 392.22 | 392.23 | 414.2 | 414.21 |
| 2-(3-hydroxy-2-oxo-4,5-dipropyl-2,5-dihydro-pyrrol-1-yl)-hexanoic acid hydroxyamide | 313.26 | 313.35 | 335.24 | 335.23 |
| 2-(3-hydroxy-2-oxo-4-phenyl-5-pyridin-2-yl-2,5-dihydro-pyrrol-1-yl)-hexanoic acid hydroxyamide | 382.21 | 382.23 | 404.19 | n.d. |
| 2-[3-(3,4-dihydroxy-phenyl)-4-hydroxy-2-methyl-5-oxo-2,5-dihydro-pyrrol-1-yl]-hexanoic acid hydroxyamide | 351.19 | 351.2 | 373.17 | 373.19 |
| 2-(3-hydroxy-2-oxo-4-propyl-5-quinolin-8-yl-2,5-dihydro-pyrrol-1-yl)-hexanoic acid hydroxyamide | 398.25 | 398.26 | 420.23 | 420.25 |
| 2-[2-(3-fluoro-4-trifluoromethyl-phenyl)-4-hydroxy-3-isopropyl-5-oxo-2,5-dihydro-pyrrol-1-yl]-hexanoic acid hydroxyamide | 433.21 | 433.23 | 455.19 | 455.21 |
| 2-(3-hydroxy-2-oxo-4-pentyl-5-pyridin-3-yl-2,5-dihydro-pyrrol-1-yl)-hexanoic acid hydroxyamide | 376.27 | 376.27 | 398.25 | n.d. |
| 2-[3-fluoro-4-hydroxy-5-oxo-2-((1E,3E)-penta-1,3-dienyl)-2,5-dihydro-pyrrol-1-yl]-hexanoic acid hydroxyamide | 313.19 | 313.18 | 335.17 | 335.2 |
| 2-[2-(4-cyano-phenyl)-4-hydroxy-5-oxo-3-propyl-2,5-dihydro-pyrrol-1-yl]-hexanoic acid hydroxyamide | 372.23 | 372.25 | 394.21 | 394.24 |

|  | calc. [M + H] | found [M + H] | calc. [M + Na] | found [M + Na] |
|---|---|---|---|---|
| 2-[2-(3-fluoro-phenyl)-4-hydroxy-5-oxo-3-propyl-2,5-dihydro-pyrrol-1-yl]-hexanoic acid hydroxyamide | 365.23 | 365.21 | 387.21 | 387.22 |
| 2-(3-hydroxy-4-isopropyl-2-oxo-5-pyridin-3-yl-2,5-dihydro-pyrrol-1-yl)-hexanoic acid hydroxyamide | 348.23 | 348.24 | 370.22 | n.d. |
| 2-(2-benzyloxymethyl-4-hydroxy-3-methylsulfanylmethyl-5-oxo-2,5-dihydro-pyrrol-1-yl)-hexanoic acid hydroxyamide | 409.23 | 409.23 | 431.21 | 431.14 |
| 2-[2-(3,4-difluoro-phenyl)-4-hydroxy-5-oxo-3-propyl-2,5-dihydro-pyrrol-1-yl]-hexanoic acid hydroxyamide | 383.22 | 383.23 | 405.2 | 405.2 |
| 2-(3-hydroxy-2-oxo-4-pentyl-5-pyridin-4-yl-2,5-dihydro-pyrrol-1-yl)-hexanoic acid hydroxyamide | 376.27 | 376.27 | 398.25 | n.d. |
| 2-[3-ethyl-2-(2-fluoro-phenyl)-4-hydroxy-5-oxo-2,5-dihydro-pyrrol-1-yl]-hexanoic acid hydroxyamide | 351.21 | 351.21 | 373.19 | 373.2 |
| 2-[3-hydroxy-4-isopropyl-2-oxo-5-(tetrahydro-furan-3-yl)-2,5-dihydro-pyrrol-1-yl]-hexanoic acid hydroxyamide | 341.26 | 341.25 | 363.24 | 363.24 |
| 2-(2-ethyl-4-hydroxy-5-oxo-3-pentyl-2,5-dihydro-pyrrol-1-yl)-hexanoic acid hydroxyamide | 327.28 | 327.27 | 349.26 | 349.25 |
| 2-(2-benzyl-4-hydroxy-3-methyl-5-oxo-2,5-dihydro-pyrrol-1-yl)-hexanoic acid hydroxyamide | 333.22 | 333.2 | 355.2 | 355.14 |
| 2-[2-(4-bromo-phenyl)-4-hydroxy-5-oxo-3-propyl-2,5-dihydro-pyrrol-1-yl]-hexanoic acid hydroxyamide | 425.15 | 425.16 | 447.13 | 447.15 |
| 2-(2-butyl-4-hydroxy-3-isopropyl-5-oxo-2,5-dihydro-pyrrol-1-yl)-hexanoic acid hydroxyamide | 327.28 | 327.27 | 349.26 | 349.35 |
| 2-[3-hydroxy-5-(1H-imidazol-2-yl)-4-(2-nitro-phenyl)-2-oxo-2,5-dihydro-pyrrol-1-yl]-hexanoic acid hydroxyamide | 416.19 | 416.2 | 438.17 | n.d. |
| 2-(2-benzyloxymethyl-4-hydroxy-5-oxo-3-propyl-2,5-dihydro-pyrrol-1-yl)-hexanoic acid hydroxyamide | 391.27 | 391.29 | 413.26 | 413.31 |
| 2-(3-ethyl-4-hydroxy-5-oxo-2-phenylethynyl-2,5-dihydro-pyrrol-1-yl)-hexanoic acid hydroxyamide | 357.22 | 357.25 | 379.2 | n.d. |
| 2-[3-ethyl-4-hydroxy-2-(2-nitro-phenyl)-5-oxo-2,5-dihydro-pyrrol-1-yl]-hexanoic acid hydroxyamide | 378.2 | 378.22 | 400.18 | 400.27 |
| 2-[3-hydroxy-4-(2-nitro-phenyl)-2-oxo-2,5-dihydro-pyrrol-1-yl]-hexanoic acid hydroxyamide | 350.16 | 350.12 | 372.15 | 372.16 |
| 2-[2-(2,3-difluoro-phenyl)-4-hydroxy-3-methyl-5-oxo-2,5-dihydro-pyrrol-1-yl]-hexanoic acid hydroxyamide | 355.18 | 355.19 | 377.16 | 377.18 |
| 2-[2-(2,3-difluoro-phenyl)-4-hydroxy-5-oxo-3-propyl-2,5-dihydro-pyrrol-1-yl]-hexanoic acid hydroxyamide | 383.22 | 383.23 | 405.2 | 405.21 |
| 2-[3-hydroxy-4-methyl-2-oxo-5-(1-phenyl-ethyl)-2,5-dihydro-pyrrol-1-yl]-hexanoic acid hydroxyamide | 347.24 | 347.24 | 369.22 | 369.23 |
| 2-[2-(3-chloro-phenyl)-4-hydroxy-3-methyl-5-oxo-2,5-dihydro-pyrrol-1-yl]-hexanoic acid hydroxyamide | 353.16 | 353.17 | 375.14 | 375.23 |
| 2-[3-hydroxy-4-(1H-indol-3-yl)-5-(1-methyl-1H-imidazol-2-yl)-2-oxo-2,5-dihydro-pyrrol-1-yl]-hexanoic acid hydroxyamide | 424.24 | 424.25 | 446.22 | n.d. |
| 2-[3-hydroxy-4-methyl-5-(2-nitro-phenyl)-2-oxo-2,5-dihydro-pyrrol-1-yl]-hexanoic acid hydroxyamide | 364.18 | 364.19 | 386.17 | 386.18 |
| 2-[3-hydroxy-4-(3-hydroxy-phenyl)-5-(1H-imidazol-2-yl)-2-oxo-2,5-dihydro-pyrrol-1-yl]-hexanoic acid hydroxyamide | 387.2 | n.d. | 409.18 | 409.21 |
| 2-[2-(3,5-dichloro-phenyl)-4-hydroxy-5-oxo-3-propyl-2,5-dihydro-pyrrol-1-yl]-hexanoic acid hydroxyamide | 415.16 | 415.18 | 437.14 | 437.15 |
| 2-[3-hydroxy-4-isopropyl-2-oxo-5-(1-oxy-pyridin-4-yl)-2,5-dihydro-pyrrol-1-yl]-hexanoic acid hydroxyamide | 364.23 | 364.23 | 386.21 | 386.23 |
| 2-(4-benzothiazol-2-yl-3-hydroxy-2-oxo-2,5-dihydro-pyrrol-1-yl)-hexanoic acid hydroxyamide | 362.15 | 362.17 | 384.13 | n.d. |
| 2-[3-hydroxy-5-((E)-3-methyl-but-1-enyl)-2-oxo-4-propyl-2,5-dihydro-pyrrol-1-yl]-hexanoic acid hydroxyamide | 339.28 | 339.29 | 361.26 | 361.24 |
| 2-[3-ethyl-2-(1-ethyl-propyl)-4-hydroxy-5-oxo-2,5-dihydro-pyrrol-1-yl]-hexanoic acid hydroxyamide | 327.28 | 327.28 | 349.26 | 349.27 |
| 2-(3-ethyl-4-hydroxy-5-oxo-2-o-tolyl-2,5-dihydro-pyrrol-1-yl)-hexanoic acid hydroxyamide | 347.24 | 347.25 | 369.22 | 369.24 |
| 2-[2-(2-fluoro-phenyl)-4-hydroxy-5-oxo-3-propyl-2,5-dihydro-pyrrol-1-yl]-hexanoic acid hydroxyamide | 365.23 | 365.31 | 387.21 | 387.23 |

-continued

| | calc. [M + H] | found [M + H] | calc. [M + Na] | found [M + Na] |
|---|---|---|---|---|
| 2-{2-[2-(4-fluoro-phenyl)-2-oxo-ethyl]-4-hydroxy-5-oxo-3-propyl-2,5-dihydro-pyrrol-1-yl}-hexanoic acid hydroxyamide | 407.24 | 407.28 | 429.22 | 429.23 |
| 2-[3-hydroxy-4-(4-hydroxy-phenyl)-5-(1H-imidazol-2-yl)-2-oxo-2,5-dihydro-pyrrol-1-yl]-hexanoic acid hydroxyamide | 387.2 | 387.21 | 409.18 | n.d. |
| 2-(3-hydroxy-4-methyl-2-oxo-5-quinolin-8-yl-2,5-dihydro-pyrrol-1-yl)-hexanoic acid hydroxyamide | 370.21 | 370.22 | 392.19 | 392.22 |
| 2-[2-(2-bromo-phenyl)-4-hydroxy-3-methyl-5-oxo-2,5-dihydro-pyrrol-1-yl]-hexanoic acid hydroxyamide | 397.11 | 397.13 | 419.09 | 419.1 |
| 2-[3-hydroxy-4-isopropyl-2-oxo-5-((E)-pent-1-enyl)-2,5-dihydro-pyrrol-1-yl]-hexanoic acid hydroxyamide | 339.28 | 339.21 | 361.26 | n.d. |
| 2-[2-(4-dimethylamino-phenyl)-4-hydroxy-3-isopropyl-5-oxo-2,5-dihydro-pyrrol-1-yl]-hexanoic acid hydroxyamide | 390.29 | 390.29 | 412.27 | n.d. |
| 2-[2-ethyl-4-hydroxy-3-(4-hydroxy-phenyl)-5-oxo-2,5-dihydro-pyrrol-1-yl]-hexanoic acid hydroxyamide | 349.22 | 349.22 | 371.2 | 371.21 |
| 2-(3-hydroxy-4-methyl-2-oxo-5-o-tolyl-2,5-dihydro-pyrrol-1-yl)-hexanoic acid hydroxyamide | 333.22 | 333.22 | 355.2 | 355.21 |
| 2-[3-hydroxy-5-(2-iodo-phenyl)-4-isopropyl-2-oxo-2,5-dihydro-pyrrol-1-yl]-hexanoic acid hydroxyamide | 473.13 | 473.14 | 495.12 | 495.13 |
| 2-[2-(2-chloro-phenyl)-4-hydroxy-5-oxo-3-propyl-2,5-dihydro-pyrrol-1-yl]-hexanoic acid hydroxyamide | 381.2 | 381.2 | 403.18 | 403.2 |
| 2-(3-hydroxy-2-oxo-4-propyl-5-pyridin-3-yl-2,5-dihydro-pyrrol-1-yl)-hexanoic acid hydroxyamide | 348.23 | 348.24 | 370.22 | n.d. |
| 2-[2-(4-chloro-phenyl)-4-hydroxy-3-isopropyl-5-oxo-2,5-dihydro-pyrrol-1-yl]-hexanoic acid hydroxyamide | 381.2 | 381.15 | 403.18 | 403.25 |
| 2-[3-hydroxy-5-(2-methylsulfanyl-ethyl)-2-oxo-4-propyl-2,5-dihydro-pyrrol-1-yl]-hexanoic acid hydroxyamide | 345.23 | 345.2 | 367.22 | 367.22 |
| 2-(3-ethyl-4-hydroxy-5-oxo-2-m-tolyl-2,5-dihydro-pyrrol-1-yl)-hexanoic acid hydroxyamide | 347.24 | 347.24 | 369.22 | 369.23 |
| 2-[2-(3,5-dichloro-phenyl)-4-hydroxy-3-methyl-5-oxo-2,5-dihydro-pyrrol-1-yl]-hexanoic acid hydroxyamide | 387.12 | 387.14 | 409.1 | n.d. |
| 2-[2-(3,5-difluoro-phenyl)-4-hydroxy-3-isopropyl-5-oxo-2,5-dihydro-pyrrol-1-yl]-hexanoic acid hydroxyamide | 383.22 | 383.3 | 405.2 | 405.21 |
| 2-[2-(3-fluoro-4-trifluoromethyl-phenyl)-4-hydroxy-5-oxo-3-propyl-2,5-dihydro-pyrrol-1-yl]-hexanoic acid hydroxyamide | 433.21 | 433.23 | 455.19 | 455.22 |
| 2-[3-hydroxy-2-oxo-5-(2-oxo-cyclohexyl)-4-propyl-2,5-dihydro-pyrrol-1-yl]-hexanoic acid hydroxyamide | 367.28 | 367.27 | 389.26 | 389.31 |
| 2-[3-ethyl-4-hydroxy-2-(2-iodo-phenyl)-5-oxo-2,5-dihydro-pyrrol-1-yl]-hexanoic acid hydroxyamide | 459.12 | 459.14 | 481.1 | n.d. |
| 2-[2-(3-fluoro-phenyl)-4-hydroxy-3-isopropyl-5-oxo-2,5-dihydro-pyrrol-1-yl]-hexanoic acid hydroxyamide | 365.23 | 365.24 | 387.21 | 387.22 |
| 2-(3-hydroxy-4-methylsulfanylmethyl-2-oxo-5-thiazol-2-yl-2,5-dihydro-pyrrol-1-yl)-hexanoic acid hydroxyamide | 372.14 | 372.17 | 394.12 | 394.15 |
| 2-[2-(4-carbamimidoyl-phenyl)-4-hydroxy-3-isopropyl-5-oxo-2,5-dihydro-pyrrol-1-yl]-hexanoic acid hydroxyamide | 389.27 | 389.27 | 411.25 | n.d. |
| 2-[3-hydroxy-5-(4-hydroxy-phenyl)-4-isopropyl-2-oxo-2,5-dihydro-pyrrol-1-yl]-hexanoic acid hydroxyamide | 363.24 | 363.26 | 385.22 | n.d. |
| 2-[2-(2,3-dichloro-phenyl)-4-hydroxy-3-isopropyl-5-oxo-2,5-dihydro-pyrrol-1-yl]-hexanoic acid hydroxyamide | 415.16 | 415.17 | 437.14 | n.d. |
| 2-[3-hydroxy-5-(5-hydroxymethyl-furan-2-yl)-4-isopropyl-2-oxo-2,5-dihydro-pyrrol-1-yl]-hexanoic acid hydroxyamide | 367.23 | 367.24 | 389.21 | n.d. |
| 2-[3-hydroxy-5-((E)-3-methyl-but-1-enyl)-2-oxo-4-phenyl-2,5-dihydro-pyrrol-1-yl]-hexanoic acid hydroxyamide | 373.26 | 373.27 | 395.24 | 395.25 |
| 2-[2-(3,5-difluoro-phenyl)-3-ethyl-4-hydroxy-5-oxo-2,5-dihydro-pyrrol-1-yl]-hexanoic acid hydroxyamide | 369.2 | 369.22 | 391.18 | 391.2 |

-continued

| | calc. [M + H] | found [M + H] | calc. [M + Na] | found [M + Na] |
|---|---|---|---|---|
| 2-(3-hydroxy-2-oxo-4-propyl-5-m-tolyl-2,5-dihydro-pyrrol-1-yl)-hexanoic acid hydroxyamide | 361.26 | 361.28 | 383.24 | 383.25 |
| 2-[2-ethyl-4-hydroxy-3-(1H-indol-3-yl)-5-oxo-2,5-dihydro-pyrrol-1-yl]-hexanoic acid hydroxyamide | 372.23 | 372.25 | 394.21 | 394.23 |
| 2-(3-hydroxy-4-isopropyl-2-oxo-5-quinolin-8-yl-2,5-dihydro-pyrrol-1-yl)-hexanoic acid hydroxyamide | 398.25 | 398.27 | 420.23 | n.d. |
| 2-[3-fluoro-4-hydroxy-5-oxo-2-(2-phenyl-propyl)-2,5-dihydro-pyrrol-1-yl]-hexanoic acid hydroxyamide | 365.23 | 365.23 | 387.21 | n.d. |
| 2-[2-(3,4-dihydroxy-phenyl)-4-hydroxy-3-isopropyl-5-oxo-2,5-dihydro-pyrrol-1-yl]-hexanoic acid hydroxyamide | 379.23 | 379.25 | 401.21 | 401.25 |
| 2-[2-(3-fluoro-4-methoxy-phenyl)-4-hydroxy-3-methyl-5-oxo-2,5-dihydro-pyrrol-1-yl]-hexanoic acid hydroxyamide | 367.2 | n.d. | 389.19 | 389.21 |
| 2-[3-hydroxy-5-(2-methylsulfanyl-ethyl)-4-methylsulfanylmethyl-2-oxo-2,5-dihydro-pyrrol-1-yl]-hexanoic acid hydroxyamide | 363.19 | 363.2 | 385.17 | 385.16 |
| 2-[2-(4-chloro-phenyl)-4-hydroxy-5-oxo-3-propyl-2,5-dihydro-pyrrol-1-yl]-hexanoic acid hydroxyamide | 381.2 | 381.2 | 403.18 | 403.18 |
| 2-[3-ethyl-2-(3-fluoro-4-trifluoromethyl-phenyl)-4-hydroxy-5-oxo-2,5-dihydro-pyrrol-1-yl]-hexanoic acid hydroxyamide | 419.19 | 419.21 | 441.17 | n.d. |
| 2-(2-benzyl-3-fluoro-4-hydroxy-5-oxo-2,5-dihydro-pyrrol-1-yl)-hexanoic acid hydroxyamide | 337.19 | 337.2 | 359.17 | 359.2 |
| 2-(3-hydroxy-4-methylsulfanylmethyl-2-oxo-5-phenethyl-2,5-dihydro-pyrrol-1-yl)-hexanoic acid hydroxyamide | 393.23 | 393.24 | 415.21 | 415.24 |
| 2-[2-(3,5-difluoro-phenyl)-4-hydroxy-5-oxo-3-propyl-2,5-dihydro-pyrrol-1-yl]-hexanoic acid hydroxyamide | 383.22 | 383.23 | 405.2 | 405.21 |
| 2-[3-hydroxy-4-methylsulfanylmethyl-5-(4-nitro-phenyl)-2-oxo-2,5-dihydro-pyrrol-1-yl]-hexanoic acid hydroxyamide | 410.17 | 410.21 | 432.16 | 432.16 |
| 2-(3-hydroxy-5-isobutyl-4-methylsulfanylmethyl-2-oxo-2,5-dihydro-pyrrol-1-yl)-hexanoic acid hydroxyamide | 345.23 | 345.23 | 367.22 | 367.26 |
| 2-[3-ethyl-4-hydroxy-2-(3-nitro-phenyl)-5-oxo-2,5-dihydro-pyrrol-1-yl]-hexanoic acid hydroxyamide | 378.2 | 378.19 | 400.18 | 400.22 |
| 2-(3-hydroxy-4-isopropyl-2-oxo-5-m-tolyl-2,5-dihydro-pyrrol-1-yl)-hexanoic acid hydroxyamide | 361.26 | n.d. | 383.24 | 383.25 |
| 2-[3-ethyl-4-hydroxy-2-(3-hydroxy-phenyl)-5-oxo-2,5-dihydro-pyrrol-1-yl]-hexanoic acid hydroxyamide | 349.22 | 349.22 | 371.2 | 371.29 |
| 2-[3-hydroxy-4-(1H-indol-3-yl)-5-(5-methyl-3H-imidazol-4-yl)-2-oxo-2,5-dihydro-pyrrol-1-yl]-hexanoic acid hydroxyamide | 424.24 | 424.26 | 446.22 | n.d. |
| 2-(3-hydroxy-2-oxo-4-pentyl-5-propyl-2,5-dihydro-pyrrol-1-yl)-hexanoic acid hydroxyamide | 341.3 | 341.29 | 363.28 | 363.21 |
| 2-[3-hydroxy-4-methylsulfanylmethyl-2-oxo-5-(tetrahydro-furan-3-yl)-2,5-dihydro-pyrrol-1-yl]-hexanoic acid hydroxyamide | 359.21 | 359.2 | 381.19 | 381.21 |
| 2-[2-(3,4-difluoro-phenyl)-4-hydroxy-3-isopropyl-5-oxo-2,5-dihydro-pyrrol-1-yl]-hexanoic acid hydroxyamide | 383.22 | 383.24 | 405.2 | 405.2 |
| 2-[2-(1,5-dimethyl-hex-4-enyl)-4-hydroxy-3-methylsulfanylmethyl-5-oxo-2,5-dihydro-pyrrol-1-yl]-hexanoic acid hydroxyamide | 399.29 | 399.28 | 421.27 | 421.28 |
| 2-[2-(4-bromo-phenyl)-4-hydroxy-3-isopropyl-5-oxo-2,5-dihydro-pyrrol-1-yl]-hexanoic acid hydroxyamide | 425.15 | 425.17 | 447.13 | n.d. |
| 2-[2-(4-chloro-phenyl)-4-hydroxy-3-methylsulfanylmethyl-5-oxo-2,5-dihydro-pyrrol-1-yl]-hexanoic acid hydroxyamide | 399.15 | 399.19 | 421.13 | 421.09 |
| 2-[2-(1,5-dimethyl-hex-4-enyl)-3-fluoro-4-hydroxy-5-oxo-2,5-dihydro-pyrrol-1-yl]-hexanoic acid hydroxyamide | 357.27 | 357.27 | 379.25 | 379.26 |
| 2-{2-[2-(4-fluoro-phenyl)-2-oxo-ethyl]-4-hydroxy-3-isopropyl-5-oxo-2,5-dihydro-pyrrol-1-yl}-hexanoic acid hydroxyamide | 407.24 | 407.33 | 429.22 | n.d. |
| 2-[3-(3,4-dihydroxy-phenyl)-4-hydroxy-5-oxo-2-(tetrahydro-furan-3-yl)-2,5-dihydro-pyrrol-1-yl]-hexanoic acid hydroxyamide | 407.22 | 407.24 | 429.21 | 429.22 |

|  | calc. [M + H] | found [M + H] | calc. [M + Na] | found [M + Na] |
|---|---|---|---|---|
| 2-[2-(3,5-dichloro-phenyl)-4-hydroxy-3-isopropyl-5-oxo-2,5-dihydro-pyrrol-1-yl]-hexanoic acid hydroxyamide | 415.16 | 415.17 | 437.14 | n.d. |
| 2-[3-(3,4-dihydroxy-phenyl)-4-hydroxy-2-(1H-imidazol-2-yl)-5-oxo-2,5-dihydro-pyrrol-1-yl]-hexanoic acid hydroxyamide | 403.19 | 403.22 | 425.18 | n.d. |
| 2-(3-hydroxy-5-hydroxymethyl-2-oxo-4-pentyl-2,5-dihydro-pyrrol-1-yl)-hexanoic acid hydroxyamide | 329.26 | 329.26 | 351.24 | n.d. |
| 2-[3-hydroxy-4-methylsulfanylmethyl-2-oxo-5-(2-oxo-cyclohexyl)-2,5-dihydro-pyrrol-1-yl]-hexanoic acid hydroxyamide | 385.23 | 385.23 | 407.21 | n.d. |
| 2-[3-ethyl-2-(3-fluoro-4-methoxy-phenyl)-4-hydroxy-5-oxo-2,5-dihydro-pyrrol-1-yl]-hexanoic acid hydroxyamide | 381.22 | 381.25 | 403.21 | 403.22 |
| 2-{3-hydroxy-4-methyl-5-[2-(5-methyl-furan-2-yl)-propyl]-2-oxo-2,5-dihydro-pyrrol-1-yl}-hexanoic acid hydroxyamide | 365.26 | 365.18 | 387.24 | 387.24 |
| 2-[3-hydroxy-5-(2-nitro-phenyl)-2-oxo-4-propyl-2,5-dihydro-pyrrol-1-yl]-hexanoic acid hydroxyamide | 392.22 | 392.25 | 414.2 | n.d. |
| 2-[3-hydroxy-2-oxo-4-phenyl-5-((E)-propenyl)-2,5-dihydro-pyrrol-1-yl]-hexanoic acid hydroxyamide | 345.22 | 345.23 | 367.2 | 367.21 |
| 2-[3-hydroxy-5-(3-hydroxy-phenyl)-4-methylsulfanylmethyl-2-oxo-2,5-dihydro-pyrrol-1-yl]-hexanoic acid hydroxyamide | 381.19 | 381.21 | 403.17 | 403.2 |
| 2-[3-hydroxy-4-isopropyl-5-(2-methylsulfanyl-ethyl)-2-oxo-2,5-dihydro-pyrrol-1-yl]-hexanoic acid hydroxyamide | 345.23 | 345.23 | 367.22 | 367.22 |
| 2-[3-fluoro-4-hydroxy-5-oxo-2-(1-phenyl-ethyl)-2,5-dihydro-pyrrol-1-yl]-hexanoic acid hydroxyamide | 351.21 | 351.22 | 373.19 | 373.2 |
| 2-(3-ethyl-4-hydroxy-5-oxo-2-pentyl-2,5-dihydro-pyrrol-1-yl)-hexanoic acid hydroxyamide | 327.28 | 327.29 | 349.26 | 349.26 |
| 2-[3-hydroxy-4-methylsulfanylmethyl-2-oxo-5-((E))-propenyl)-2,5-dihydro-pyrrol-1-yl]-hexanoic acid hydroxyamide | 329.19 | 329.2 | 351.18 | n.d. |
| 2-[3-fluoro-4-hydroxy-2-(3-nitro-phenyl)-5-oxo-2,5-dihydro-pyrrol-1-yl]-hexanoic acid hydroxyamide | 368.15 | 368.19 | 390.13 | 390.17 |
| 2-[3-hydroxy-4-methylsulfanylmethyl-2-oxo-5-(2-phenyl-propyl)-2,5-dihydro-pyrrol-1-yl]-hexanoic acid hydroxyamide | 407.25 | 407.31 | 429.23 | n.d. |
| 2-[3-fluoro-4-hydroxy-5-oxo-2-(4-pyridin-2-yl-phenyl)-2,5-dihydro-pyrrol-1-yl]-hexanoic acid hydroxyamide | 400.2 | 400.21 | 422.18 | n.d. |
| 2-[3-fluoro-4-hydroxy-2-(4-nitro-phenyl)-5-oxo-2,5-dihydro-pyrrol-1-yl]-hexanoic acid hydroxyamide | 368.15 | 368.24 | 390.13 | n.d. |
| 2-(3-hydroxy-4-isopropyl-2-oxo-5-pentyl-2,5-dihydro-pyrrol-1-yl)-hexanoic acid hydroxyamide | 341.3 | 341.3 | 363.28 | 363.26 |
| 2-[3-hydroxy-4-isopropyl-2-oxo-5-(1-phenyl-ethyl)-2,5-dihydro-pyrrol-1-yl]-hexanoic acid hydroxyamide | 375.28 | 375.27 | 397.26 | n.d. |
| 2-[2-(4-carbamimidoyl-phenyl)-4-hydroxy-5-oxo-3-phenyl-2,5-dihydro-pyrrol-1-yl]-hexanoic acid hydroxyamide | 423.24 | 423.25 | 445.23 | n.d. |
| 2-(3-hydroxy-2-oxo-4-pentyl-5-thiophen-3-yl-2,5-dihydro-pyrrol-1-yl)-hexanoic acid hydroxyamide | 381.23 | 381.24 | 403.21 | n.d. |
| 2-[3-hydroxy-2-oxo-5-(1-oxo-1,2,3,4-tetrahydro-naphthalen-2-yl)-4-propyl-2,5-dihydro-pyrrol-1-yl]-hexanoic acid hydroxyamide | 415.27 | 415.27 | 437.26 | 437.24 |
| 2-(2-benzyloxymethyl-3-ethyl-4-hydroxy-5-oxo-2,5-dihydro-pyrrol-1-yl)-hexanoic acid hydroxyamide | 377.25 | 377.28 | 399.24 | n.d. |
| 2-[3-hydroxy-4-methylsulfanylmethyl-2-oxo-5-(1-oxo-1,2,3,4-tetrahydro-naphthalen-2-yl)-2,5-dihydro-pyrrol-1-yl]-hexanoic acid hydroxyamide | 433.23 | 433.23 | 455.21 | n.d. |
| 2-(3-hydroxy-2-oxo-4-phenyl-5-propyl-2,5-dihydro-pyrrol-1-yl)-hexanoic acid hydroxyamide | 347.24 | 347.24 | 369.22 | 369.22 |
| 2-(3-hydroxy-2-oxo-4-propyl-5-thiophen-3-yl-2,5-dihydro-pyrrol-1-yl)-hexanoic acid hydroxyamide | 353.19 | 353.21 | 375.18 | 375.18 |
| 2-(3-hydroxy-2-oxo-4-pentyl-5-phenethyl-2,5-dihydro-pyrrol-1-yl)-hexanoic acid hydroxyamide | 403.32 | 403.25 | 425.3 | 425.27 |
| 2-[2-(3-fluoro-4-methoxy-phenyl)-4-hydroxy-3-methylsulfanylmethyl-5-oxo-2,5-dihydro-pyrrol-1-yl]-hexanoic acid hydroxyamide | 413.19 | 413.2 | 435.18 | n.d. |
| 2-[2-(1-ethyl-propyl)-4-hydroxy-5-oxo-3-propyl-2,5-dihydro-pyrrol-1-yl]-hexanoic acid hydroxyamide | 341.3 | 341.29 | 363.28 | 363.26 |
| 2-{2-[(E)-2-(4-dimethylamino-phenyl)-vinyl]-4-hydroxy-3-methylsulfanylmethyl-5-oxo-2,5-dihydro-pyrrol-1-yl}-hexanoic acid hydroxyamide | 434.26 | 434.25 | 456.25 | n.d. |

| | calc. [M + H] | found [M + H] | calc. [M + Na] | found [M + Na] |
|---|---|---|---|---|
| 2-(3-hydroxy-2-oxo-4-phenyl-5-thiophen-3-yl-2,5-dihydro-pyrrol-1-yl)-hexanoic acid hydroxyamide | 387.17 | 387.17 | 409.15 | 409.17 |
| 2-[3-hydroxy-2-oxo-4-pentyl-5-((E)-propenyl)-2,5-dihydro-pyrrol-1-yl]-hexanoic acid hydroxyamide | 339.28 | 339.28 | 361.26 | n.d. |
| 2-(2-benzofuran-2-yl-4-hydroxy-3-methylsulfanylmethyl-5-oxo-2,5-dihydro-pyrrol-1-yl)-hexanoic acid hydroxyamide | 405.19 | 405.18 | 427.17 | n.d. |
| 2-{2-[(E)-2-(4-dimethylamino-phenyl)-vinyl]-4-hydroxy-3-methyl-5-oxo-2,5-dihydro-pyrrol-1-yl}-hexanoic acid hydroxyamide | 388.27 | 388.26 | 410.25 | n.d. |
| 2-[3-hydroxy-2-oxo-5-((1E,3E)-penta-1,3-dienyl)-4-propyl-2,5-dihydro-pyrrol-1-yl]-hexanoic acid hydroxyamide | 337.26 | 337.25 | 359.24 | n.d. |
| 2-[3-hydroxy-2-oxo-5-((E)-pent-1-enyl)-4-propyl-2,5-dihydro-pyrrol-1-yl]-hexanoic acid hydroxyamide | 339.28 | 339.32 | 361.26 | n.d. |
| 2-[3-hydroxy-4-isopropyl-5-(1-methyl-butyl)-2-oxo-2,5-dihydro-pyrrol-1-yl]-hexanoic acid hydroxyamide | 341.3 | 341.26 | 363.28 | 363.26 |
| 2-[3-hydroxy-4-(4-hydroxy-phenyl)-5-(5-methyl-3H-imidazol-4-yl)-2-oxo-2,5-dihydro-pyrrol-1-yl]-hexanoic acid hydroxyamide | 401.22 | 401.22 | 423.2 | n.d. |
| 2-[3-hydroxy-5-(6-methyl-pyridin-2-yl)-2-oxo-4-propyl-2,5-dihydro-pyrrol-1-yl]-hexanoic acid hydroxyamide | 362.25 | 362.25 | 384.24 | n.d. |
| 2-[3-hydroxy-4-(3-hydroxy-phenyl)-5-(5-methyl-3H-imidazol-4-yl)-2-oxo-2,5-dihydro-pyrrol-1-yl]-hexanoic acid hydroxyamide | 401.22 | 401.23 | 423.2 | n.d. |
| 2-[2-(3-chloro-phenyl)-3-fluoro-4-hydroxy-5-oxo-2,5-dihydro-pyrrol-1-yl]-hexanoic acid hydroxyamide | 357.13 | 357.14 | 379.11 | 379.13 |
| 2-[3-hydroxy-4-(3-hydroxy-phenyl)-2-oxo-5-propyl-2,5-dihydro-pyrrol-1-yl]-hexanoic acid hydroxyamide | 363.24 | 363.23 | 385.22 | 385.23 |
| 2-(2-benzyl-4-hydroxy-5-oxo-3-propyl-2,5-dihydro-pyrrol-1-yl)-hexanoic acid hydroxyamide | 361.26 | 361.19 | 383.24 | 383.23 |
| 2-(3-hydroxy-2-oxo-4-phenyl-5-thiophen-2-yl-2,5-dihydro-pyrrol-1-yl)-hexanoic acid hydroxyamide | 387.17 | 387.19 | 409.15 | 409.18 |
| 2-[3-hydroxy-5-(2-methylsulfanyl-ethyl)-2-oxo-4-phenyl-2,5-dihydro-pyrrol-1-yl]-hexanoic acid hydroxyamide | 379.21 | 379.21 | 401.19 | 401.2 |
| 2-[3-hydroxy-4-(1H-indol-3-yl)-2-oxo-5-pyridin-4-yl-2,5-dihydro-pyrrol-1-yl]-hexanoic acid hydroxyamide | 421.22 | 421.23 | 443.21 | n.d. |
| 2-[3-hydroxy-4-(1H-indol-3-yl)-2-oxo-5-pyridin-2-yl-2,5-dihydro-pyrrol-1-yl]-hexanoic acid hydroxyamide | 421.22 | 421.24 | 443.21 | n.d. |
| 2-(3-hydroxy-2-oxo-4-propyl-5-o-tolyl-2,5-dihydro-pyrrol-1-yl)-hexanoic acid hydroxyamide | 361.26 | 361.25 | 383.24 | n.d. |
| 2-[3-ethyl-4-hydroxy-2-(1-methyl-1H-imidazol-2-yl)-5-oxo-2,5-dihydro-pyrrol-1-yl]-hexanoic acid hydroxyamide | 337.23 | 337.22 | 359.21 | n.d. |
| 2-(3-hydroxy-5-isobutyl-2-oxo-4-propyl-2,5-dihydro-pyrrol-1-yl)-hexanoic acid hydroxyamide | 327.28 | 327.27 | 349.26 | n.d. |
| 2-(3-hydroxy-2-oxo-4-phenyl-5-pyridin-3-yl-2,5-dihydro-pyrrol-1-yl)-hexanoic acid hydroxyamide | 382.21 | 382.22 | 404.19 | n.d. |
| 2-[3-(3,4-dihydroxy-phenyl)-2-ethyl-4-hydroxy-5-oxo-2,5-dihydro-pyrrol-1-yl]-hexanoic acid hydroxyamide | 365.21 | 365.14 | 387.19 | 387.19 |
| 2-[3-hydroxy-4-isopropyl-5-(2-nitro-phenyl)-2-oxo-2,5-dihydro-pyrrol-1-yl]-hexanoic acid hydroxyamide | 392.22 | 392.22 | 414.2 | n.d. |
| 2-[3-hydroxy-5-(5-methyl-3H-imidazol-4-yl)-4-(2-nitro-phenyl)-2-oxo-2,5-dihydro-pyrrol-1-yl]-hexanoic acid hydroxyamide | 430.21 | 430.23 | 452.19 | n.d. |
| 2-(2-butyl-4-hydroxy-5-oxo-3-propyl-2,5-dihydro-pyrrol-1-yl)-hexanoic acid hydroxyamide | 327.28 | 327.25 | 349.26 | 349.27 |
| 2-[3-hydroxy-5-(3-nitro-phenyl)-2-oxo-4-propyl-2,5-dihydro-pyrrol-1-yl]-hexanoic acid hydroxyamide | 392.22 | 392.22 | 414.2 | 414.21 |
| 2-[3-ethyl-4-hydroxy-5-oxo-2-((E)-pent-1-enyl)-2,5-dihydro-pyrrol-1-yl]-hexanoic acid hydroxyamide | 325.26 | 325.27 | 347.24 | n.d. |
| 2-[2-(3-fluoro-phenyl)-4-hydroxy-5-oxo-3-phenyl-2,5-dihydro-pyrrol-1-yl]-hexanoic acid hydroxyamide | 399.21 | 399.22 | 421.19 | 421.15 |

| | calc. [M + H] | found [M + H] | calc. [M + Na] | found [M + Na] |
|---|---|---|---|---|
| 2-[3-hydroxy-4-(4-hydroxy-phenyl)-2-oxo-5-pyridin-4-yl-2,5-dihydro-pyrrol-1-yl]-hexanoic acid hydroxyamide | 398.21 | 398.21 | 420.19 | n.d. |
| 2-[3-hydroxy-4-(4-hydroxy-phenyl)-2-oxo-5-pyridin-2-yl-2,5-dihydro-pyrrol-1-yl]-hexanoic acid hydroxyamide | 398.21 | 398.2 | 420.19 | n.d. |
| 2-[2-(4-chloro-3-trifluoromethyl-phenyl)-4-hydroxy-5-oxo-3-phenyl-2,5-dihydro-pyrrol-1-yl]-hexanoic acid hydroxyamide | 483.16 | 483.19 | 505.14 | 505.17 |
| 2-[2-(4-carbamimidoyl-phenyl)-4-hydroxy-3-methylsulfanylmethyl-5-oxo-2,5-dihydro-pyrrol-1-yl]-hexanoic acid hydroxyamide | 407.22 | 407.23 | 429.2 | n.d. |
| 2-[3-(3,4-dihydroxy-phenyl)-4-hydroxy-2-(5-methyl-3H-imidazol-4-yl)-5-oxo-2,5-dihydro-pyrrol-1-yl]-hexanoic acid hydroxyamide | 417.21 | 417.23 | 439.2 | n.d. |
| 2-[2-(2-chloro-phenyl)-4-hydroxy-3-isopropyl-5-oxo-2,5-dihydro-pyrrol-1-yl]-hexanoic acid hydroxyamide | 381.2 | 381.19 | 403.18 | 403.19 |
| 2-[3-hydroxy-4-(3-hydroxy-phenyl)-2-oxo-5-pyridin-2-yl-2,5-dihydro-pyrrol-1-yl]-hexanoic acid hydroxyamide | 398.21 | 398.21 | 420.19 | n.d. |
| 2-[3-hydroxy-4-(3-hydroxy-phenyl)-2-oxo-5-pyridin-4-yl-2,5-dihydro-pyrrol-1-yl]-hexanoic acid hydroxyamide | 398.21 | 398.22 | 420.19 | n.d. |
| 2-(3-hydroxy-4-isopropyl-2-oxo-5-phenyl-2,5-dihydro-pyrrol-1-yl)-hexanoic acid hydroxyamide | 347.24 | 347.24 | 369.22 | 369.14 |
| 2-(3-hydroxy-4-isopropyl-2-oxo-5-o-tolyl-2,5-dihydro-pyrrol-1-yl)-hexanoic acid hydroxyamide | 361.26 | 361.32 | 383.24 | 383.23 |
| 2-[3-hydroxy-2-oxo-5-(1-oxy-pyridin-4-yl)-4-propyl-2,5-dihydro-pyrrol-1-yl]-hexanoic acid hydroxyamide | 364.23 | 364.22 | 386.21 | n.d. |
| 2-[3-hydroxy-4-(2-nitro-phenyl)-2-oxo-5-pyridin-4-yl-2,5-dihydro-pyrrol-1-yl]-hexanoic acid hydroxyamide | 427.19 | 427.21 | 449.18 | n.d. |
| 2-[2-(3,4-difluoro-phenyl)-4-hydroxy-5-oxo-3-phenyl-2,5-dihydro-pyrrol-1-yl]-hexanoic acid hydroxyamide | 417.2 | 417.22 | 439.18 | 439.19 |
| 2-[2-cyclopropyl-4-hydroxy-3-(3-hydroxy-phenyl)-5-oxo-2,5-dihydro-pyrrol-1-yl]-hexanoic acid hydroxyamide | 361.22 | 361.21 | 383.2 | n.d. |
| 2-[3-hydroxy-4-(2-nitro-phenyl)-2-oxo-5-pyridin-2-yl-2,5-dihydro-pyrrol-1-yl]-hexanoic acid hydroxyamide | 427.19 | 427.21 | 449.18 | n.d. |
| 2-[2-(2,3-difluoro-phenyl)-4-hydroxy-5-oxo-3-phenyl-2,5-dihydro-pyrrol-1-yl]-hexanoic acid hydroxyamide | 417.2 | 417.21 | 439.18 | 439.19 |
| 2-[2-(4-fluoro-phenyl)-4-hydroxy-5-oxo-3-phenyl-2,5-dihydro-pyrrol-1-yl]-hexanoic acid hydroxyamide | 399.21 | 399.21 | 421.19 | 421.22 |
| 2-(2-furan-2-yl-4-hydroxy-3-methylsulfanylmethyl-5-oxo-2,5-dihydro-pyrrol-1-yl)-hexanoic acid hydroxyamide | 355.17 | 355.22 | 377.15 | 377.09 |
| 2-[2-(4,5-dimethyl-furan-2-yl)-4-hydroxy-5-oxo-3-propyl-2,5-dihydro-pyrrol-1-yl]-hexanoic acid hydroxyamide | 365.26 | 365.28 | 387.24 | 387.22 |
| 2-(3-hydroxy-2-oxo-5-phenyl-4-propyl-2,5-dihydro-pyrrol-1-yl)-hexanoic acid hydroxyamide | 347.24 | 347.23 | 369.22 | 369.22 |
| 2-[3-hydroxy-4-(4-hydroxy-phenyl)-2-oxo-5-propyl-2,5-dihydro-pyrrol-1-yl]-hexanoic acid hydroxyamide | 363.24 | 363.23 | 385.22 | 385.16 |
| 2-(2-furan-2-yl-4-hydroxy-5-oxo-3-pentyl-2,5-dihydro-pyrrol-1-yl)-hexanoic acid hydroxyamide | 365.26 | 365.24 | 387.24 | n.d. |
| 2-[2-(4-carbamimidoyl-phenyl)-4-hydroxy-5-oxo-3-pentyl-2,5-dihydro-pyrrol-1-yl]-hexanoic acid hydroxyamide | 417.3 | 417.38 | 439.29 | n.d. |
| 2-[2-(4-fluoro-phenyl)-4-hydroxy-3-isopropyl-5-oxo-2,5-dihydro-pyrrol-1-yl]-hexanoic acid hydroxyamide | 365.23 | 365.23 | 387.21 | 387.22 |
| 2-[3-hydroxy-5-(1H-imidazol-2-yl)-2-oxo-4-propyl-2,5-dihydro-pyrrol-1-yl]-hexanoic acid hydroxyamide | 337.23 | 337.21 | 359.21 | n.d. |
| 2-(2-cyclopropyl-4-hydroxy-5-oxo-3-propyl-2,5-dihydro-pyrrol-1-yl)-hexanoic acid hydroxyamide | 311.24 | 311.23 | 333.22 | 333.2 |
| 2-[3-hydroxy-4-methyl-5-(5-methyl-2,4-dioxo-3,4-dihydro-2H-pyrimidin-1-ylmethyl)-2-oxo-2,5-dihydro-pyrrol-1-yl]-hexanoic acid hydroxyamide | 381.22 | 381.21 | 403.2 | 403.2 |

-continued

| | calc. [M + H] | found [M + H] | calc. [M + Na] | found [M + Na] |
|---|---|---|---|---|
| 2-[2-cyclopropyl-4-hydroxy-3-(2-nitro-phenyl)-5-oxo-2,5-dihydro-pyrrol-1-yl]-hexanoic acid hydroxyamide | 390.2 | 390.21 | 412.18 | n.d. |
| 2-(3-hydroxy-2-oxo-4-pentyl-5-thiazol-2-yl-2,5-dihydro-pyrrol-1-yl)-hexanoic acid hydroxyamide | 382.23 | 382.3 | 404.21 | 404.18 |
| 2-[3-hydroxy-5-(1H-imidazol-2-yl)-2-oxo-4-pentyl-2,5-dihydro-pyrrol-1-yl]-hexanoic acid hydroxyamide | 365.27 | 365.25 | 387.25 | n.d. |
| 2-(2-benzyl-4-hydroxy-5-oxo-3-phenyl-2,5-dihydro-pyrrol-1-yl)-hexanoic acid hydroxyamide | 395.24 | 395.23 | 417.22 | 417.22 |
| 2-[3-hydroxy-5-hydroxymethyl-4-(2-nitro-phenyl)-2-oxo-2,5-dihydro-pyrrol-1-yl]-hexanoic acid hydroxyamide | 380.18 | 380.18 | 402.16 | n.d. |
| 2-(3-hydroxy-4-methylsulfanylmethyl-2-oxo-5-pyridin-3-yl-2,5-dihydro-pyrrol-1-yl)-hexanoic acid hydroxyamide | 366.19 | 366.19 | 388.17 | n.d. |
| 2-[2-cyclopropyl-4-hydroxy-3-(1H-indol-3-yl)-5-oxo-2,5-dihydro-pyrrol-1-yl]-hexanoic acid hydroxyamide | 384.23 | 384.22 | 406.21 | 406.22 |
| 2-[3-hydroxy-5-(5-methyl-furan-2-yl)-2-oxo-4-pentyl-2,5-dihydro-pyrrol-1-yl]-hexanoic acid hydroxyamide | 379.27 | 379.26 | 401.26 | 401.23 |
| 2-(3-hydroxy-5-hydroxymethyl-4-methyl-2-oxo-2,5-dihydro-pyrrol-1-yl)-hexanoic acid hydroxyamide | 273.18 | 273.16 | 295.16 | 295.15 |
| 2-[2-(3-bromo-phenyl)-4-hydroxy-3-methyl-5-oxo-2,5-dihydro-pyrrol-1-yl]-hexanoic acid hydroxyamide | 397.11 | 397.1 | 419.09 | n.d. |
| 2-[3-hydroxy-4-(1H-indol-3-yl)-5-isobutyl-2-oxo-2,5-dihydro-pyrrol-1-yl]-hexanoic acid hydroxyamide | 400.27 | 400.26 | 422.25 | 422.24 |
| 2-[2-(3-fluoro-phenyl)-4-hydroxy-5-oxo-3-pentyl-2,5-dihydro-pyrrol-1-yl]-hexanoic acid hydroxyamide | 393.27 | 393.26 | 415.25 | n.d. |
| 2-[2-(3-bromo-phenyl)-4-hydroxy-3-(2-nitro-phenyl)-5-oxo-2,5-dihydro-pyrrol-1-yl]-hexanoic acid hydroxyamide | 504.11 | 504.12 | 526.09 | 526.1 |
| 2-(3-hydroxy-5-isobutyl-2-oxo-4-phenyl-2,5-dihydro-pyrrol-1-yl)-hexanoic acid hydroxyamide | 361.26 | 361.24 | 383.24 | 383.23 |
| 2-(3-hydroxy-2-oxo-4-phenyl-5-quinolin-2-yl-2,5-dihydro-pyrrol-1-yl)-hexanoic acid hydroxyamide | 432.23 | 432.23 | 454.21 | 454.2 |
| 2-(2-sec-butyl-4-hydroxy-3-isopropyl-5-oxo-2,5-dihydro-pyrrol-1-yl)-hexanoic acid hydroxyamide | 327.28 | n.d. | 349.26 | 349.24 |
| 2-(3-hydroxy-4-methyl-2-oxo-5-thiophen-3-yl-2,5-dihydro-pyrrol-1-yl)-hexanoic acid hydroxyamide | 325.15 | 325.15 | 347.14 | 347.14 |
| 2-[2-(3-bromo-4-methoxy-phenyl)-4-hydroxy-3-isopropyl-5-oxo-2,5-dihydro-pyrrol-1-yl]-hexanoic acid hydroxyamide | 455.16 | 455.17 | 477.14 | 477.15 |
| 2-(2-sec-butyl-4-hydroxy-5-oxo-3-pentyl-2,5-dihydro-pyrrol-1-yl)-hexanoic acid hydroxyamide | 355.32 | 355.32 | 377.3 | 377.27 |
| 2-[3-hydroxy-4-(2-nitro-phenyl)-2-oxo-5-quinolin-2-yl-2,5-dihydro-pyrrol-1-yl]-hexanoic acid hydroxyamide | 477.21 | 477.23 | 499.19 | n.d. |
| 2-[2-(2-chloro-phenyl)-4-hydroxy-3-methylsulfanylmethyl-5-oxo-2,5-dihydro-pyrrol-1-yl]-hexanoic acid hydroxyamide | 399.15 | 399.15 | 421.13 | 421.15 |
| 2-[3-hydroxy-4-(3-hydroxy-phenyl)-5-isobutyl-2-oxo-2,5-dihydro-pyrrol-1-yl]-hexanoic acid hydroxyamide | 377.25 | 377.25 | 399.24 | 399.22 |
| 2-[2-(3-bromo-phenyl)-4-hydroxy-3-methylsulfanylmethyl-5-oxo-2,5-dihydro-pyrrol-1-yl]-hexanoic acid hydroxyamide | 443.1 | 443.11 | 465.08 | 465.11 |
| 2-[2-(4-carbamimidoyl-phenyl)-3-fluoro-4-hydroxy-5-oxo-2,5-dihydro-pyrrol-1-yl]-hexanoic acid hydroxyamide | 365.19 | 365.2 | 387.18 | n.d. |
| 2-[3-hydroxy-5-(5-methyl-furan-2-yl)-4-(2-nitro-phenyl)-2-oxo-2,5-dihydro-pyrrol-1-yl]-hexanoic acid hydroxyamide | 430.2 | 430.2 | 452.18 | n.d. |
| 2-[3-hydroxy-4-(1H-indol-3-yl)-2-oxo-5-thiazol-2-yl-2,5-dihydro-pyrrol-1-yl]-hexanoic acid hydroxyamide | 427.18 | 427.19 | 449.16 | 449.17 |
| 2-[2-(2-fluoro-phenyl)-4-hydroxy-5-oxo-3-pentyl-2,5-dihydro-pyrrol-1-yl]-hexanoic acid hydroxyamide | 393.27 | 393.26 | 415.25 | 415.28 |
| 2-[2-(2-fluoro-phenyl)-4-hydroxy-5-oxo-3-phenyl-2,5-dihydro-pyrrol-1-yl]-hexanoic acid hydroxyamide | 399.21 | 399.22 | 421.19 | 421.2 |
| 2-[2-(4-carbamimidoyl-phenyl)-3-ethyl-4-hydroxy-5-oxo-2,5-dihydro-pyrrol-1-yl]-hexanoic acid hydroxyamide | 375.25 | 375.25 | 397.23 | n.d. |

-continued

| | calc. [M + H] | found [M + H] | calc. [M + Na] | found [M + Na] |
|---|---|---|---|---|
| 2-[2-(3-fluoro-phenyl)-4-hydroxy-3-methylsulfanylmethyl-5-oxo-2,5-dihydro-pyrrol-1-yl]-hexanoic acid hydroxyamide | 383.18 | 383.18 | 405.16 | 405.18 |
| 2-[2-(2-fluoro-phenyl)-4-hydroxy-3-isopropyl-5-oxo-2,5-dihydro-pyrrol-1-yl]-hexanoic acid hydroxyamide | 365.23 | 365.22 | 387.21 | 387.21 |
| 2-[2-furan-2-yl-4-hydroxy-3-(2-nitro-phenyl)-5-oxo-2,5-dihydro-pyrrol-1-yl]-hexanoic acid hydroxyamide | 416.18 | 416.19 | 438.16 | n.d. |
| 2-[2-(2-chloro-quinolin-3-yl)-4-hydroxy-3-(2-nitro-phenyl)-5-oxo-2,5-dihydro-pyrrol-1-yl]-hexanoic acid hydroxyamide | 511.17 | 511.2 | 533.15 | n.d. |
| 2-[3-hydroxy-5-(5-methyl-furan-2-yl)-4-methylsulfanylmethyl-2-oxo-2,5-dihydro-pyrrol-1-yl]-hexanoic acid hydroxyamide | 369.19 | 369.2 | 391.17 | 391.18 |
| 2-[2-(2-chloro-phenyl)-4-hydroxy-5-oxo-3-phenyl-2,5-dihydro-pyrrol-1-yl]-hexanoic acid hydroxyamide | 415.18 | 415.19 | 437.16 | 437.18 |
| 2-[3-hydroxy-2-oxo-4-phenyl-5-(tetrahydro-furan-3-yl)-2,5-dihydro-pyrrol-1-yl]-hexanoic acid hydroxyamide | 375.23 | 375.23 | 397.22 | 397.22 |
| 2-[2-cyclopropyl-4-hydroxy-3-(4-hydroxy-phenyl)-5-oxo-2,5-dihydro-pyrrol-1-yl]-hexanoic acid hydroxyamide | 361.22 | 361.22 | 383.2 | 383.2 |
| 2-[2-benzofuran-2-yl-4-hydroxy-3-(1H-indol-3-yl)-5-oxo-2,5-dihydro-pyrrol-1-yl]-hexanoic acid hydroxyamide | 460.22 | 460.23 | 482.21 | n.d. |
| 2-[2-(2-fluoro-phenyl)-4-hydroxy-3-methylsulfanylmethyl-5-oxo-2,5-dihydro-pyrrol-1-yl]-hexanoic acid hydroxyamide | 383.18 | 383.19 | 405.16 | 405.17 |
| 2-[3-hydroxy-4-(1H-indol-3-yl)-2-oxo-5-thiophen-3-yl-2,5-dihydro-pyrrol-1-yl]-hexanoic acid hydroxyamide | 426.18 | 426.21 | 448.17 | 448.19 |
| 2-[2-(2-chloro-phenyl)-4-hydroxy-3-(2-nitro-phenyl)-5-oxo-2,5-dihydro-pyrrol-1-yl]-hexanoic acid hydroxyamide | 460.16 | 460.18 | 482.14 | 482.18 |
| 2-[2-benzofuran-2-yl-4-hydroxy-3-(3-hydroxy-phenyl)-5-oxo-2,5-dihydro-pyrrol-1-yl]-hexanoic acid hydroxyamide | 437.21 | 437.22 | 459.19 | 459.21 |
| 2-[3-hydroxy-2-(4-hydroxy-phenyl)-2-oxo-4-phenyl-2,5-dihydro-pyrrol-1-yl]-hexanoic acid hydroxyamide | 397.21 | 397.23 | 419.2 | n.d. |
| 2-[2-(3-bromo-4-methoxy-phenyl)-4-hydroxy-5-oxo-3-phenyl-2,5-dihydro-pyrrol-1-yl]-hexanoic acid hydroxyamide | 489.14 | n.d. | 511.12 | 511.14 |
| 2-[3-hydroxy-4-(2-nitro-phenyl)-2-oxo-5-(tetrahydro-furan-3-yl)-2,5-dihydro-pyrrol-1-yl]-hexanoic acid hydroxyamide | 420.22 | 420.21 | 442.2 | 442.21 |
| 2-[3-hydroxy-4-(4-hydroxy-phenyl)-2-oxo-5-m-tolyl-2,5-dihydro-pyrrol-1-yl]-hexanoic acid hydroxyamide | 411.23 | 411.23 | 433.22 | 433.22 |
| 2-[2-(4-carbamimidoyl-phenyl)-4-hydroxy-3-(2-nitro-phenyl)-5-oxo-2,5-dihydro-pyrrol-1-yl]-hexanoic acid hydroxyamide | 468.23 | 468.22 | 490.21 | n.d. |
| 2-[3-hydroxy-2-oxo-5-(2-oxo-cyclohexyl)-4-phenyl-2,5-dihydro-pyrrol-1-yl]-hexanoic acid hydroxyamide | 401.25 | 401.26 | 423.24 | 423.25 |
| 2-[2-(3-bromo-4-methoxy-phenyl)-4-hydroxy-3-methyl-5-oxo-2,5-dihydro-pyrrol-1-yl]-hexanoic acid hydroxyamide | 427.12 | 427.12 | 449.11 | n.d. |
| 2-(3-hydroxy-5-hydroxymethyl-2-oxo-4-phenyl-2,5-dihydro-pyrrol-1-yl)-hexanoic acid hydroxyamide | 335.2 | 335.2 | 357.18 | 357.18 |
| 2-[3-hydroxy-4-(1H-indol-3-yl)-5-(5-methyl-2,4-dioxo-3,4-dihydro-2H-pyrimidin-1-ylmethyl)-2-oxo-2,5-dihydro-pyrrol-1-yl]-hexanoic acid hydroxyamide | 482.24 | 482.25 | 504.23 | 504.23 |
| 2-[3-ethyl-4-hydroxy-2-(1H-imidazol-2-yl)-5-oxo-2,5-dihydro-pyrrol-1-yl]-hexanoic acid hydroxyamide | 323.21 | 323.22 | 345.19 | n.d. |
| 2-(2-tert-butyl-4-hydroxy-5-oxo-3-phenyl-2,5-dihydro-pyrrol-1-yl)-hexanoic acid hydroxyamide | 361.26 | 361.25 | 383.24 | 383.23 |
| 2-(3-fluoro-4-hydroxy-5-oxo-2-thiazol-2-yl-2,5-dihydro-pyrrol-1-yl)-hexanoic acid hydroxyamide | 330.12 | 330.12 | 352.1 | 352.11 |
| 2-(3-hydroxy-5-isopropyl-2-oxo-4-propyl-2,5-dihydro-pyrrol-1-yl)-hexanoic acid hydroxyamide | 313.26 | 313.24 | 335.24 | 335.23 |

| | calc. [M + H] | found [M + H] | calc. [M + Na] | found [M + Na] |
|---|---|---|---|---|
| 2-[3-hydroxy-4-(4-hydroxy-phenyl)-2-oxo-5-pyridin-3-yl-2,5-dihydro-pyrrol-1-yl]-hexanoic acid hydroxyamide | 398.21 | 398.21 | 420.19 | n.d. |
| 2-(3-hydroxy-2-oxo-4-pentyl-5-m-tolyl-2,5-dihydro-pyrrol-1-yl)-hexanoic acid hydroxyamide | 389.3 | 389.29 | 411.28 | 411.27 |
| 2-[3-hydroxy-4-(1H-indol-3-yl)-5-(5-methyl-furan-2-yl)-2-oxo-2,5-dihydro-pyrrol-1-yl]-hexanoic acid hydroxyamide | 424.23 | 424.22 | 446.21 | n.d. |
| 2-[2-(2-fluoro-phenyl)-4-hydroxy-3-(2-nitro-phenyl)-5-oxo-2,5-dihydro-pyrrol-1-yl]-hexanoic acid hydroxyamide | 444.19 | 444.2 | 466.17 | 466.19 |
| 2-(2-furan-2-yl-4-hydroxy-5-oxo-3-propyl-2,5-dihydro-pyrrol-1-yl)-hexanoic acid hydroxyamide | 337.22 | 337.29 | 359.2 | 359.2 |
| 2-(3-hydroxy-4-methylsulfanylmethyl-2-oxo-5-quinolin-2-yl-2,5-dihydro-pyrrol-1-yl)-hexanoic acid hydroxyamide | 416.2 | 416.2 | 438.19 | n.d. |
| 2-(2-tert-butyl-4-hydroxy-5-oxo-3-propyl-2,5-dihydro-pyrrol-1-yl)-hexanoic acid hydroxyamide | 327.28 | 327.28 | 349.26 | 349.25 |
| 2-[2-(2-chloro-phenyl)-4-hydroxy-3-(1H-indol-3-yl)-5-oxo-2,5-dihydro-pyrrol-1-yl]-hexanoic acid hydroxyamide | 454.19 | 454.2 | 476.17 | 476.18 |
| 2-[3-fluoro-4-hydroxy-2-(5-methyl-2,4-dioxo-3,4-dihydro-2H-pyrimidin-1-ylmethyl)-5-oxo-2,5-dihydro-pyrrol-1-yl]-hexanoic acid hydroxyamide | 385.18 | 385.19 | 407.17 | 407.18 |
| 2-[3-hydroxy-4-(4-hydroxy-phenyl)-2-oxo-5-quinolin-2-yl-2,5-dihydro-pyrrol-1-yl]-hexanoic acid hydroxyamide | 448.22 | 448.23 | 470.21 | n.d. |
| 2-[3-benzothiazol-2-yl-4-hydroxy-2-(1H-imidazol-2-yl)-5-oxo-2,5-dihydro-pyrrol-1-yl]-hexanoic acid hydroxyamide | 428.17 | 428.18 | 450.15 | n.d. |
| 2-[3-hydroxy-5-(5-methyl-2,4-dioxo-3,4-dihydro-2H-pyrimidin-1-ylmethyl)-2-oxo-4-propyl-2,5-dihydro-pyrrol-1-yl]-hexanoic acid hydroxyamide | 409.25 | 409.25 | 431.24 | 431.25 |
| 2-[3-hydroxy-4-methylsulfanylmethyl-2-oxo-5-(2-trifluoromethyl-phenyl)-2,5-dihydro-pyrrol-1-yl]-hexanoic acid hydroxyamide | 433.18 | 433.18 | 455.16 | 455.17 |
| 2-[3-hydroxy-5-(5-methyl-furan-2-yl)-2-oxo-4-phenyl-2,5-dihydro-pyrrol-1-yl]-hexanoic acid hydroxyamide | 385.21 | 385.22 | 407.2 | 407.2 |
| 2-(3-hydroxy-5-hydroxymethyl-4-isopropyl-2-oxo-2,5-dihydro-pyrrol-1-yl)-hexanoic acid hydroxyamide | 301.22 | 301.21 | 323.2 | 323.18 |
| 2-[2-(3-fluoro-phenyl)-4-hydroxy-3-(4-hydroxy-phenyl)-5-oxo-2,5-dihydro-pyrrol-1-yl]-hexanoic acid hydroxyamide | 415.2 | 415.21 | 437.18 | 437.18 |
| 2-(3-ethyl-4-hydroxy-5-oxo-2-thiophen-2-yl-2,5-dihydro-pyrrol-1-yl)-hexanoic acid hydroxyamide | 339.17 | n.d. | 361.16 | 361.11 |
| 2-[2-(2-chloro-phenyl)-3-ethyl-4-hydroxy-5-oxo-2,5-dihydro-pyrrol-1-yl]-hexanoic acid hydroxyamide | 367.18 | 367.19 | 389.16 | 389.16 |
| 2-[2-(3-bromo-4-methoxy-phenyl)-4-hydroxy-5-oxo-3-propyl-2,5-dihydro-pyrrol-1-yl]-hexanoic acid hydroxyamide | 455.16 | 455.16 | 477.14 | n.d. |
| 2-[3-hydroxy-2-oxo-4-phenyl-5-(2-trifluoromethyl-phenyl)-2,5-dihydro-pyrrol-1-yl]-hexanoic acid hydroxyamide | 449.2 | 449.22 | 471.18 | 471.21 |
| 2-(2-sec-butyl-4-hydroxy-5-oxo-3-phenyl-2,5-dihydro-pyrrol-1-yl)-hexanoic acid hydroxyamide | 361.26 | 361.19 | 383.24 | 383.25 |
| 2-[2-(1-ethyl-propyl)-4-hydroxy-5-oxo-3-pentyl-2,5-dihydro-pyrrol-1-yl]-hexanoic acid hydroxyamide | 369.34 | 369.31 | 391.32 | 391.3 |
| 2-[3-hydroxy-4-(2-nitro-phenyl)-2-oxo-5-thiophen-2-yl-2,5-dihydro-pyrrol-1-yl]-hexanoic acid hydroxyamide | 432.15 | 432.15 | 454.14 | n.d. |
| 2-[3-hydroxy-5-hydroxymethyl-4-(4-hydroxy-phenyl)-2-oxo-2,5-dihydro-pyrrol-1-yl]-hexanoic acid hydroxyamide | 351.19 | 351.18 | 373.17 | n.d. |
| 2-(3-hydroxy-2-oxo-4-phenyl-5-thiazol-2-yl-2,5-dihydro-pyrrol-1-yl)-hexanoic acid hydroxyamide | 388.16 | 388.16 | 410.15 | 410.13 |
| 2-[2-(2-fluoro-phenyl)-4-hydroxy-3-(1H-indol-3-yl)-5-oxo-2,5-dihydro-pyrrol-1-yl]-hexanoic acid hydroxyamide | 438.22 | 438.23 | 460.2 | 460.21 |
| 2-[2-furan-2-yl-4-hydroxy-3-(1H-indol-3-yl)-5-oxo-2,5-dihydro-pyrrol-1-yl]-hexanoic acid hydroxyamide | 410.21 | 410.21 | 432.19 | 432.11 |
| 2-[2-(3-fluoro-phenyl)-4-hydroxy-3-(1H-indol-3-yl)-5-oxo-2,5-dihydro-pyrrol-1-yl]-hexanoic acid hydroxyamide | 438.22 | 438.23 | 460.2 | 460.21 |

-continued

|  | calc. [M + H] | found [M + H] | calc. [M + Na] | found [M + Na] |
|---|---|---|---|---|
| 2-[2-(4-carbamimidoyl-phenyl)-4-hydroxy-3-(1H-indol-3-yl)-5-oxo-2,5-dihydro-pyrrol-1-yl]-hexanoic acid hydroxyamide | 462.26 | 462.26 | 484.24 | n.d. |
| 2-[2-(2-chloro-phenyl)-4-hydroxy-3-(3-hydroxy-phenyl)-5-oxo-2,5-dihydro-pyrrol-1-yl]-hexanoic acid hydroxyamide | 431.17 | 431.11 | 453.15 | 453.17 |
| 2-[3-hydroxy-4-(3-hydroxy-phenyl)-2-oxo-5-pyridin-3-yl-2,5-dihydro-pyrrol-1-yl]-hexanoic acid hydroxyamide | 398.21 | 398.21 | 420.19 | n.d. |
| 2-[3-hydroxy-5-(5-methyl-2,4-dioxo-3,4-dihydro-2H-pyrimidin-1-ylmethyl)-2-oxo-4-phenyl-2,5-dihydro-pyrrol-1-yl]-hexanoic acid hydroxyamide | 443.23 | 443.24 | 465.22 | 465.31 |
| 2-(3-benzothiazol-2-yl-4-hydroxy-5-oxo-2-quinolin-2-yl-2,5-dihydro-pyrrol-1-yl]-hexanoic acid hydroxyamide | 489.19 | 489.21 | 511.18 | n.d. |
| 2-(3-hydroxy-4-methylsulfanylmethyl-2-oxo-5-m-tolyl-2,5-dihydro-pyrrol-1-yl)-hexanoic acid hydroxyamide | 379.21 | 379.2 | 401.19 | 401.19 |
| 2-(3-ethyl-4-hydroxy-2-hydroxymethyl-5-oxo-2,5-dihydro-pyrrol-1-yl)-hexanoic acid hydroxyamide | 287.2 | 287.18 | 309.18 | 309.18 |
| 2-[3-hydroxy-4-isopropyl-2-oxo-5-(2-oxo-cyclohexyl)-2,5-dihydro-pyrrol-1-yl]-hexanoic acid hydroxyamide | 367.28 | 367.27 | 389.26 | 389.24 |
| 2-[3-hydroxy-4,5-bis-(1H-indol-3-yl)-2-oxo-2,5-dihydro-pyrrol-1-yl]-hexanoic acid hydroxyamide | 459.24 | 459.24 | 481.22 | n.d. |
| 2-[2-furan-2-yl-4-hydroxy-3-(4-hydroxy-phenyl)-5-oxo-2,5-dihydro-pyrrol-1-yl]-hexanoic acid hydroxyamide | 387.19 | 387.19 | 409.17 | 409.19 |
| 2-[3-hydroxy-4-(3-hydroxy-phenyl)-2-oxo-5-(2-oxo-cyclohexyl)-2,5-dihydro-pyrrol-1-yl]-hexanoic acid hydroxyamide | 417.25 | 417.24 | 439.23 | n.d. |
| 2-[3-hydroxy-4-(1H-indol-3-yl)-2-oxo-5-m-tolyl-2,5-dihydro-pyrrol-1-yl]-hexanoic acid hydroxyamide | 434.25 | 434.27 | 456.23 | 456.3 |
| 2-[3-hydroxy-2-oxo-5-(2-oxo-cyclohexyl)-4-pentyl-2,5-dihydro-pyrrol-1-yl]-hexanoic acid hydroxyamide | 395.31 | 395.3 | 417.3 | 417.3 |
| 2-[2-benzyl-4-hydroxy-3-(1H-indol-3-yl)-5-oxo-2,5-dihydro-pyrrol-1-yl]-hexanoic acid hydroxyamide | 434.25 | 434.26 | 456.23 | 456.26 |
| 2-[2-benzyl-4-hydroxy-3-(4-hydroxy-phenyl)-5-oxo-2,5-dihydro-pyrrol-1-yl]-hexanoic acid hydroxyamide | 411.23 | 411.24 | 433.22 | 433.22 |
| 2-(2-benzofuran-2-yl-4-hydroxy-5-oxo-3-phenyl-2,5-dihydro-pyrrol-1-yl)-hexanoic acid hydroxyamide | 421.21 | 421.23 | 443.19 | 443.22 |
| 2-[2-furan-2-yl-4-hydroxy-3-(3-hydroxy-phenyl)-5-oxo-2,5-dihydro-pyrrol-1-yl]-hexanoic acid hydroxyamide | 387.19 | 387.19 | 409.17 | 409.19 |
| 2-[3-hydroxy-4-(3-hydroxy-phenyl)-2-oxo-5-quinolin-2-yl-2,5-dihydro-pyrrol-1-yl]-hexanoic acid hydroxyamide | 448.22 | 448.23 | 470.21 | n.d. |
| 2-[3-fluoro-4-hydroxy-2-(2-hydroxy-naphthalen-1-yl)-5-oxo-2,5-dihydro-pyrrol-1-yl]-hexanoic acid hydroxyamide | 389.18 | 389.19 | 411.16 | n.d. |
| 2-[3-hydroxy-5-(2-hydroxy-naphthalen-1-yl)-2-oxo-4-propyl-2,5-dihydro-pyrrol-1-yl]-hexanoic acid hydroxyamide | 413.25 | 413.26 | 435.24 | n.d. |
| 2-[2-(2-chloro-quinolin-3-yl)-4-hydroxy-5-oxo-3-phenyl-2,5-dihydro-pyrrol-1-yl]-hexanoic acid hydroxyamide | 466.19 | 466.19 | 488.17 | n.d. |
| 2-(2-furan-2-yl-4-hydroxy-5-oxo-3-phenyl-2,5-dihydro-pyrrol-1-yl)-hexanoic acid hydroxyamide | 371.19 | 371.2 | 393.18 | 393.18 |
| 2-(3-hydroxy-2-oxo-4-pentyl-5-quinolin-2-yl-2,5-dihydro-pyrrol-1-yl)-hexanoic acid hydroxyamide | 426.29 | 426.3 | 448.27 | 448.27 |
| 2-(2-benzofuran-2-yl-3-ethyl-4-hydroxy-5-oxo-2,5-dihydro-pyrrol-1-yl)-hexanoic acid hydroxyamide | 373.21 | 373.22 | 395.2 | 395.2 |
| 2-[3-hydroxy-5-(1H-indol-3-yl)-2-oxo-4-pentyl-2,5-dihydro-pyrrol-1-yl]-hexanoic acid hydroxyamide | 414.29 | 414.36 | 436.27 | n.d. |
| 2-[3-hydroxy-4-isopropyl-2-oxo-5-(1-oxo-1,2,3,4-tetrahydro-naphthalen-2-yl)-2,5-dihydro-pyrrol-1-yl]-hexanoic acid hydroxyamide | 415.27 | 415.28 | 437.26 | n.d. |
| 2-(3-hydroxy-5-isobutyl-2-oxo-4-pentyl-2,5-dihydro-pyrrol-1-yl)-hexanoic acid hydroxyamide | 355.32 | 355.3 | 377.3 | 377.28 |
| 2-[3-hydroxy-4-(4-hydroxy-phenyl)-5-isopropyl-2-oxo-2,5-dihydro-pyrrol-1-yl]-hexanoic acid hydroxyamide | 363.24 | 363.22 | 385.22 | 385.21 |

-continued

| | calc. [M + H] | found [M + H] | calc. [M + Na] | found [M + Na] |
|---|---|---|---|---|
| 2-[3-hydroxy-4-(3-hydroxy-phenyl)-2-oxo-5-thiophen-3-yl-2,5-dihydro-pyrrol-1-yl]-hexanoic acid hydroxyamide | 403.17 | 403.17 | 425.15 | 425.15 |
| 2-[3-hydroxy-4-(1H-indol-3-yl)-2-oxo-5-thiophen-2-yl-2,5-dihydro-pyrrol-1-yl]-hexanoic acid hydroxyamide | 426.18 | 426.18 | 448.17 | 448.18 |
| 2-[2-(1-ethyl-propyl)-4-hydroxy-5-oxo-3-phenyl-2,5-dihydro-pyrrol-1-yl]-hexanoic acid hydroxyamide | 375.28 | 375.25 | 397.26 | 397.22 |
| 2-(3-fluoro-4-hydroxy-2-hydroxymethyl-5-oxo-2,5-dihydro-pyrrol-1-yl)-hexanoic acid hydroxyamide | 277.15 | 277.14 | 299.13 | n.d. |
| 2-[2-(2-chloro-quinolin-3-yl)-4-hydroxy-3-(4-hydroxy-phenyl)-5-oxo-2,5-dihydro-pyrrol-1-yl]-hexanoic acid hydroxyamide | 482.18 | 482.19 | 504.17 | n.d. |
| 2-(3-hydroxy-4-methylsulfanylmethyl-2-oxo-5-thiophen-3-yl-2,5-dihydro-pyrrol-1-yl)-hexanoic acid hydroxyamide | 371.15 | 371.15 | 393.13 | n.d. |
| 2-[3-hydroxy-4-(4-hydroxy-phenyl)-2-oxo-5-thiophen-3-yl-2,5-dihydro-pyrrol-1-yl]-hexanoic acid hydroxyamide | 403.17 | 403.17 | 425.15 | 425.16 |
| 2-(2-benzyl-4-hydroxy-5-oxo-3-pentyl-2,5-dihydro-pyrrol-1-yl)-hexanoic acid hydroxyamide | 389.3 | 389.28 | 411.28 | 411.26 |
| 2-[2-benzofuran-2-yl-4-hydroxy-3-(2-nitro-phenyl)-5-oxo-2,5-dihydro-pyrrol-1-yl]-hexanoic acid hydroxyamide | 466.19 | 466.2 | 488.18 | 488.19 |
| 2-[2-(2-fluoro-phenyl)-4-hydroxy-3-methyl-5-oxo-2,5-dihydro-pyrrol-1-yl]-hexanoic acid hydroxyamide | 337.19 | 337.18 | 359.17 | 359.17 |
| 2-[2-(1-ethyl-propyl)-4-hydroxy-3-(1H-indol-3-yl)-5-oxo-2,5-dihydro-pyrrol-1-yl]-hexanoic acid hydroxyamide | 414.29 | 414.28 | 436.27 | 436.26 |
| 2-[2-(4-carbamimidoyl-phenyl)-4-hydroxy-3-(4-hydroxy-phenyl)-5-oxo-2,5-dihydro-pyrrol-1-yl]-hexanoic acid hydroxyamide | 439.24 | 439.23 | 461.22 | n.d. |
| 2-[3-fluoro-4-hydroxy-5-oxo-2-(2-oxo-cyclohexyl)-2,5-dihydro-pyrrol-1-yl]-hexanoic acid hydroxyamide | 343.2 | 343.2 | 365.19 | n.d. |
| 2-(3-ethyl-2-furan-2-yl-4-hydroxy-5-oxo-2,5-dihydro-pyrrol-1-yl)-hexanoic acid hydroxyamide | 323.2 | 323.19 | 345.18 | 345.17 |
| 2-(2-benzofuran-2-yl-4-hydroxy-5-oxo-3-pentyl-2,5-dihydro-pyrrol-1-yl)-hexanoic acid hydroxyamide | 415.27 | 415.26 | 437.26 | 437.25 |
| 2-[3-hydroxy-4-(3-hydroxy-phenyl)-2-oxo-5-m-tolyl-2,5-dihydro-pyrrol-1-yl]-hexanoic acid hydroxyamide | 411.23 | 411.23 | 433.22 | 433.21 |
| 2-[3-hydroxy-4-(2-nitro-phenyl)-2-oxo-5-thiazol-2-yl-2,5-dihydro-pyrrol-1-yl]-hexanoic acid hydroxyamide | 433.15 | 433.15 | 455.13 | 455.12 |
| 2-[2-(2-chloro-quinolin-3-yl)-4-hydroxy-3-methyl-5-oxo-2,5-dihydro-pyrrol-1-yl]-hexanoic acid hydroxyamide | 404.17 | 404.18 | 426.15 | n.d. |
| 2-[2-(3-bromo-4-methoxy-phenyl)-4-hydroxy-3-(1H-indol-3-yl)-5-oxo-2,5-dihydro-pyrrol-1-yl]-hexanoic acid hydroxyamide | 528.15 | 528.15 | 550.13 | n.d. |
| 2-[2-(2-fluoro-phenyl)-4-hydroxy-3-(3-hydroxy-phenyl)-5-oxo-2,5-dihydro-pyrrol-1-yl]-hexanoic acid hydroxyamide | 415.2 | 415.21 | 437.18 | 437.18 |
| 2-[2-(1-ethyl-propyl)-4-hydroxy-3-(2-nitro-phenyl)-5-oxo-2,5-dihydro-pyrrol-1-yl]-hexanoic acid hydroxyamide | 420.26 | 420.26 | 442.24 | 442.23 |
| 2-[2-(3-bromo-phenyl)-4-hydroxy-3-(3-hydroxy-phenyl)-5-oxo-2,5-dihydro-pyrrol-1-yl]-hexanoic acid hydroxyamide | 475.12 | 475.15 | 497.1 | n.d. |
| 2-[3-hydroxy-4-(4-hydroxy-phenyl)-5-isobutyl-2-oxo-2,5-dihydro-pyrrol-1-yl]-hexanoic acid hydroxyamide | 377.25 | 377.24 | 399.24 | 399.24 |
| 2-[3-hydroxy-4-(4-hydroxy-phenyl)-2-oxo-5-(2-oxo-cyclohexyl)-2,5-dihydro-pyrrol-1-yl]-hexanoic acid hydroxyamide | 417.25 | 417.25 | 439.23 | n.d. |
| 2-[3-hydroxy-4-(4-hydroxy-phenyl)-5-(5-methyl-furan-2-yl)-2-oxo-2,5-dihydro-pyrrol-1-yl]-hexanoic acid hydroxyamide | 401.21 | 401.22 | 423.19 | 423.2 |
| 2-(2-sec-butyl-4-hydroxy-3-methyl-5-oxo-2,5-dihydro-pyrrol-1-yl)-hexanoic acid hydroxyamide | 299.24 | n.d. | 321.22 | 321.2 |
| 2-[3-hydroxy-4-(2-nitro-phenyl)-2-oxo-5-thiophen-3-yl-2,5-dihydro-pyrrol-1-yl]-hexanoic acid hydroxyamide | 432.15 | 432.17 | 454.14 | 454.14 |

-continued

| | calc. [M + H] | found [M + H] | calc. [M + Na] | found [M + Na] |
|---|---|---|---|---|
| 2-[3-hydroxy-5-(4-hydroxy-phenyl)-4-(2-nitro-phenyl)-2-oxo-2,5-dihydro-pyrrol-1-yl]-hexanoic acid hydroxyamide | 442.2 | 442.22 | 464.18 | n.d. |
| 2-[3-hydroxy-2-oxo-5-(1-oxo-1,2,3,4-tetrahydro-naphthalen-2-yl)-4-pentyl-2,5-dihydro-pyrrol-1-yl]-hexanoic acid hydroxyamide | 443.31 | 443.3 | 465.29 | n.d. |
| 2-[3-hydroxy-4-(3-hydroxy-phenyl)-2-oxo-5-thiazol-2-yl-2,5-dihydro-pyrrol-1-yl]-hexanoic acid hydroxyamide | 404.16 | 404.17 | 426.14 | n.d. |
| 2-[2-(3-fluoro-phenyl)-4-hydroxy-3-(3-hydroxy-phenyl)-5-oxo-2,5-dihydro-pyrrol-1-yl]-hexanoic acid hydroxyamide | 415.2 | 415.21 | 437.18 | 437.19 |
| 2-[2-(3-bromo-phenyl)-4-hydroxy-5-oxo-3-phenyl-2,5-dihydro-pyrrol-1-yl]-hexanoic acid hydroxyamide | 459.13 | 459.13 | 481.11 | 481.14 |
| 2-[2-(3-fluoro-phenyl)-4-hydroxy-3-(2-nitro-phenyl)-5-oxo-2,5-dihydro-pyrrol-1-yl]-hexanoic acid hydroxyamide | 444.19 | 444.19 | 466.17 | 466.17 |
| 2-[3-hydroxy-4-(3-hydroxy-phenyl)-5-(5-methyl-furan-2-yl)-2-oxo-2,5-dihydro-pyrrol-1-yl]-hexanoic acid hydroxyamide | 401.21 | 401.22 | 423.19 | 423.19 |
| 2-[3-hydroxy-4-(1H-indol-3-yl)-2-oxo-5-(2-oxo-cyclohexyl)-2,5-dihydro-pyrrol-1-yl]-hexanoic acid hydroxyamide | 440.27 | 440.27 | 462.25 | 462.24 |
| 2-[3-hydroxy-4-(1H-indol-3-yl)-5-(4-nitro-phenyl)-2-oxo-2,5-dihydro-pyrrol-1-yl]-hexanoic acid hydroxyamide | 465.21 | 465.22 | 487.19 | 487.2 |
| 2-[2-(4-carbamimidoyl-phenyl)-4-hydroxy-5-oxo-3-propyl-2,5-dihydro-pyrrol-1-yl]-hexanoic acid hydroxyamide | 389.27 | 389.25 | 411.25 | n.d. |
| 2-[3-hydroxy-5-(1H-imidazol-2-yl)-4-isopropyl-2-oxo-2,5-dihydro-pyrrol-1-yl]-hexanoic acid hydroxyamide | 337.23 | 337.21 | 359.21 | n.d. |
| 2-(2-cyclopropyl-4-hydroxy-5-oxo-3-phenyl-2,5-dihydro-pyrrol-1-yl)-hexanoic acid hydroxyamide | 345.22 | 345.23 | 367.2 | 367.13 |
| 2-[2-(2,3-dihydroxy-phenyl)-4-hydroxy-3-(1H-indol-3-yl)-5-oxo-2,5-dihydro-pyrrol-1-yl]-hexanoic acid hydroxyamide | 452.22 | 452.22 | 474.2 | 474.21 |
| 2-[3-hydroxy-5-(4-nitro-phenyl)-2-oxo-4-phenyl-2,5-dihydro-pyrrol-1-yl]-hexanoic acid hydroxyamide | 426.2 | 426.2 | 448.18 | 448.19 |
| 2-(3-hydroxy-5-hydroxymethyl-2-oxo-4-propyl-2,5-dihydro-pyrrol-1-yl)-hexanoic acid hydroxyamide | 301.22 | 301.2 | 323.2 | 323.18 |
| 2-[2-tert-butyl-4-hydroxy-3-(4-hydroxy-phenyl)-5-oxo-2,5-dihydro-pyrrol-1-yl]-hexanoic acid hydroxyamide | 377.25 | 377.24 | 399.24 | n.d. |
| 2-[3-hydroxy-5-hydroxymethyl-4-(1H-indol-3-yl)-2-oxo-2,5-dihydro-pyrrol-1-yl]-hexanoic acid hydroxyamide | 374.21 | n.d. | 396.19 | 396.19 |
| 2-[3-hydroxy-4-(1H-indol-3-yl)-2-oxo-5-quinolin-2-yl-2,5-dihydro-pyrrol-1-yl]-hexanoic acid hydroxyamide | 471.24 | 471.25 | 493.22 | n.d. |
| 2-(3-hydroxy-5-isobutyl-4-isopropyl-2-oxo-2,5-dihydro-pyrrol-1-yl)-hexanoic acid hydroxyamide | 327.28 | 327.26 | 349.26 | 349.24 |
| 2-[3-hydroxy-4-(4-hydroxy-phenyl)-2-oxo-5-thiophen-2-yl-2,5-dihydro-pyrrol-1-yl]-hexanoic acid hydroxyamide | 403.17 | 403.18 | 425.15 | 425.16 |
| 2-[2-(2,3-dihydroxy-phenyl)-4-hydroxy-5-oxo-3-propyl-2,5-dihydro-pyrrol-1-yl]-hexanoic acid hydroxyamide | 379.23 | 379.23 | 401.21 | 401.21 |
| 2-[3-hydroxy-4-isopropyl-5-(5-methyl-furan-2-yl)-2-oxo-2,5-dihydro-pyrrol-1-yl]-hexanoic acid hydroxyamide | 351.24 | 351.23 | 373.22 | 373.22 |
| 2-[2-(2-fluoro-phenyl)-4-hydroxy-3-(4-hydroxy-phenyl)-5-oxo-2,5-dihydro-pyrrol-1-yl]-hexanoic acid hydroxyamide | 415.2 | 415.22 | 437.18 | 437.2 |
| 2-[3-hydroxy-4-(1H-indol-3-yl)-5-(2-methylsutfanyl-ethyl)-2-oxo-2,5-dihydro-pyrrol-1-yl]-hexanoic acid hydroxyamide | 418.22 | 418.25 | 440.21 | 440.21 |
| 2-[2-(2-chloro-phenyl)-4-hydroxy-3-(4-hydroxy-phenyl)-5-oxo-2,5-dihydro-pyrrol-1-yl]-hexanoic acid hydroxyamide | 431.17 | 431.19 | 453.15 | 453.17 |
| 2-(3-hydroxy-2-oxo-4-propyl-5-thiophen-2-yl-2,5-dihydro-pyrrol-1-yl)-hexanoic acid hydroxyamide | 353.19 | 353.21 | 375.18 | 375.18 |
| 2-[3-hydroxy-4-methyl-5-(5-methyl-furan-2-yl)-2-oxo-2,5-dihydro-pyrrol-1-yl]-hexanoic acid hydroxyamide | 323.2 | 323.2 | 345.18 | 345.18 |

| | calc. [M + H] | found [M + H] | calc. [M + Na] | found [M + Na] |
|---|---|---|---|---|
| 2-(3-benzothiazol-2-yl-4-hydroxy-5-oxo-2-pyridin-4-yl-2,5-dihydro-pyrrol-1-yl)-hexanoic acid hydroxyamide | 439.18 | 439.2 | 461.16 | n.d. |
| 2-[2-(3-chloro-phenyl)-4-hydroxy-3-(2-nitro-phenyl)-5-oxo-2,5-dihydro-pyrrol-1-yl]-hexanoic acid hydroxyamide | 460.16 | 460.17 | 482.14 | 482.16 |
| 2-[2-(2,3-dimethoxy-phenyl)-4-hydroxy-3-isopropyl-5-oxo-2,5-dihydro-pyrrol-1-yl]-hexanoic acid hydroxyamide | 407.27 | 407.26 | 429.25 | 429.24 |
| 2-[3-hydroxy-4-(3-hydroxy-phenyl)-2-oxo-5-thiophen-2-yl-2,5-dihydro-pyrrol-1-yl]-hexanoic acid hydroxyamide | 403.17 | 403.18 | 425.15 | 425.15 |
| 2-[3-hydroxy-4-(3-hydroxy-phenyl)-2-oxo-5-(3,4,5-trimethoxy-phenyl)-2,5-dihydro-pyrrol-1-yl]-hexanoic acid hydroxyamide | 487.26 | 487.26 | 509.24 | 509.25 |
| 2-[2-benzyl-4-hydroxy-3-(2-nitro-phenyl)-5-oxo-2,5-dihydro-pyrrol-1-yl]-hexanoic acid hydroxyamide | 440.22 | 440.23 | 462.2 | 462.19 |
| 2-[3-fluoro-4-hydroxy-2-(4-hydroxy-phenyl)-5-oxo-2,5-dihydro-pyrrol-1-yl]-hexanoic acid hydroxyamide | 339.16 | 339.22 | 361.15 | n.d. |
| 2-[3-hydroxy-4-(1H-indol-3-yl)-2-oxo-5-(3,4,5-trimethoxy-phenyl)-2,5-dihydro-pyrrol-1-yl]-hexanoic acid hydroxyamide | 510.27 | 510.27 | 532.25 | 532.26 |
| 2-[2-(2,3-dimethoxy-phenyl)-4-hydroxy-3-(4-hydroxy-phenyl)-5-oxo-2,5-dihydro-pyrrol-1-yl]-hexanoic acid hydroxyamide | 457.24 | 457.24 | 479.22 | 479.23 |
| 2-[3-hydroxy-4-(4-hydroxy-phenyl)-2-oxo-5-(3,4,5-trimethoxy-phenyl)-2,5-dihydro-pyrrol-1-yl]-hexanoic acid hydroxyamide | 487.26 | 487.26 | 509.24 | 509.25 |
| 2-[3-hydroxy-4-(1H-indol-3-yl)-5-isopropyl-2-oxo-2,5-dihydro-pyrrol-1-yl]-hexanoic acid hydroxyamide | 386.25 | 386.25 | 408.23 | 408.24 |
| 2-[2-benzyl-4-hydroxy-3-(3-hydroxy-phenyl)-5-oxo-2,5-dihydro-pyrrol-1-yl]-hexanoic acid hydroxyamide | 411.23 | 411.24 | 433.22 | 433.23 |
| 2-(3-hydroxy-2-oxo-4-pentyl-5-o-tolyl-2,5-dihydro-pyrrol-1-yl)-hexanoic acid hydroxyamide | 389.3 | 389.3 | 411.28 | 411.27 |
| 2-[2-benzofuran-2-yl-4-hydroxy-3-(4-hydroxy-phenyl)-5-oxo-2,5-dihydro-pyrrol-1-yl]-hexanoic acid hydroxyamide | 437.21 | 437.22 | 459.19 | n.d. |
| 2-[2-(3-bromo-phenyl)-4-hydroxy-3-(1H-indol-3-yl)-5-oxo-2,5-dihydro-pyrrol-1-yl]-hexanoic acid hydroxyamide | 498.14 | 498.23 | 520.12 | 520.14 |
| 2-[3-hydroxy-4-(2-nitro-phenyl)-2-oxo-5-m-tolyl-2,5-dihydro-pyrrol-1-yl]-hexanoic acid hydroxyamide | 440.22 | 440.23 | 462.2 | 462.21 |
| 2-(3-hydroxy-2-oxo-4-phenyl-5-o-tolyl-2,5-dihydro-pyrrol-1-yl)-hexanoic acid hydroxyamide | 395.24 | 395.25 | 417.22 | 417.23 |
| 2-[3-fluoro-4-hydroxy-2-(5-methyl-3H-imidazol-4-yl)-5-oxo-2,5-dihydro-pyrrol-1-yl]-hexanoic acid hydroxyamide | 327.18 | 327.25 | 349.16 | n.d. |
| 2-(3-benzothiazol-2-yl-4-hydroxy-5-oxo-2-pyridin-3-yl-2,5-dihydro-pyrrol-1-yl)-hexanoic acid hydroxyamide | 439.18 | 439.19 | 461.16 | n.d. |
| 2-[3-hydroxy-5-(2-methylsulfanyl-ethyl)-2-oxo-4-pentyl-2,5-dihydro-pyrrol-1-yl]-hexanoic acid hydroxyamide | 373.27 | 373.17 | 395.25 | 395.24 |
| 2-(3-hydroxy-2-oxo-4-phenyl-5-m-tolyl-2,5-dihydro-pyrrol-1-yl)-hexanoic acid hydroxyamide | 395.24 | 395.23 | 417.22 | 417.22 |
| 2-[2-(4-carbamimidoyl-phenyl)-4-hydroxy-3-(3-hydroxy-phenyl)-5-oxo-2,5-dihydro-pyrrol-1-yl]-hexanoic acid hydroxyamide | 439.24 | 439.24 | 461.22 | n.d. |
| 2-[3-fluoro-4-hydroxy-2-(5-methyl-furan-2-yl)-5-oxo-2,5-dihydro-pyrrol-1-yl]-hexanoic acid hydroxyamide | 327.17 | n.d. | 349.15 | 349.17 |
| 2-[2-(2,3-dimethoxy-phenyl)-4-hydroxy-3-(1H-indol-3-yl)-5-oxo-2,5-dihydro-pyrrol-1-yl]-hexanoic acid hydroxyamide | 480.26 | 480.26 | 502.24 | 502.26 |
| 2-[3-hydroxy-5-(2-hydroxy-5-methoxy-phenyl)-4-(4-hydroxy-phenyl)-2-oxo-2,5-dihydro-pyrrol-1-yl]-hexanoic acid hydroxyamide | 443.22 | 443.23 | 465.2 | 465.22 |
| 2-(2-tert-butyl-4-hydroxy-5-oxo-3-phenyl-2,5-dihydro-pyrrol-1-yl)-hexanoic acid hydroxyamide | 355.32 | 355.3 | 377.3 | 377.29 |
| 2-(2-cyclopropyl-3-fluoro-4-hydroxy-5-oxo-2,5-dihydro-pyrrol-1-yl)-hexanoic acid hydroxyamide | 287.17 | 287.18 | 309.15 | 309.23 |

-continued

| | calc. [M + H] | found [M + H] | calc. [M + Na] | found [M + Na] |
|---|---|---|---|---|
| 2-[3-hydroxy-4-(2-nitro-phenyl)-2-oxo-5-(3,4,5-trimethoxy-phenyl)-2,5-dihydro-pyrrol-1-yl]-hexanoic acid hydroxyamide | 516.24 | 516.25 | 538.22 | 538.3 |
| 2-[3-hydroxy-5-(2-hydroxy-5-methoxy-phenyl)-4-methyl-2-oxo-2,5-dihydro-pyrrol-1-yl]-hexanoic acid hydroxyamide | 365.21 | 365.22 | 387.19 | n.d. |
| 2-[3-hydroxy-5-(2-hydroxy-5-methoxy-phenyl)-4-isopropyl-2-oxo-2,5-dihydro-pyrrol-1-yl]-hexanoic acid hydroxyamide | 393.25 | n.d. | 415.23 | 415.25 |
| 2-[3-hydroxy-4-isopropyl-2-oxo-5-(3,4,5-trimethoxy-phenyl)-2,5-dihydro-pyrrol-1-yl]-hexanoic acid hydroxyamide | 437.28 | 437.28 | 459.26 | 459.27 |
| 2-(3-hydroxy-5-isobutyl-4-methyl-2-oxo-2,5-dihydro-pyrrol-1-yl)-hexanoic acid hydroxyamide | 299.24 | 299.24 | 321.22 | 321.21 |
| 2-[3-hydroxy-2-oxo-4-propyl-5-(3,4,5-trimethoxy-phenyl)-2,5-dihydro-pyrrol-1-yl]-hexanoic acid hydroxyamide | 437.28 | 437.28 | 459.26 | 459.35 |
| 2-[3-hydroxy-5-(2-hydroxy-5-methoxy-phenyl)-2-oxo-4-phenyl-2,5-dihydro-pyrrol-1-yl]-hexanoic acid hydroxyamide | 427.23 | 427.24 | 449.21 | 449.22 |
| 2-[3-hydroxy-4,5-bis-(4-hydroxy-phenyl)-2-oxo-2,5-dihydro-pyrrol-1-yl]-hexanoic acid hydroxyamide | 413.21 | 413.2 | 435.19 | 435.2 |
| 2-[3-hydroxy-5-isobutyl-4-(2-nitro-phenyl)-2-oxo-2,5-dihydro-pyrrol-1-yl]-hexanoic acid hydroxyamide | 406.24 | 406.24 | 428.22 | 428.23 |
| 2-[2-(1-ethyl-propyl)-4-hydroxy-3-(4-hydroxy-phenyl)-5-oxo-2,5-dihydro-pyrrol-1-yl]-hexanoic acid hydroxyamide | 391.27 | 391.29 | 413.26 | 413.27 |
| 2-[3-hydroxy-5-(2-hydroxy-naphthalen-1-yl)-4-isopropyl-2-oxo-2,5-dihydro-pyrrol-1-yl]-hexanoic acid hydroxyamide | 413.25 | 413.28 | 435.24 | n.d. |
| 2-[3-hydroxy-4-(4-hydroxy-phenyl)-2-oxo-5-thiazol-2-yl-2,5-dihydro-pyrrol-1-yl]-hexanoic acid hydroxyamide | 404.16 | 404.18 | 426.14 | 426.16 |
| 2-[2-(2,3-dihydroxy-phenyl)-4-hydroxy-5-oxo-3-phenyl-2,5-dihydro-pyrrol-1-yl]-hexanoic acid hydroxyamide | 413.21 | 413.31 | 435.19 | n.d. |
| 2-[3-hydroxy-4-(2-nitro-phenyl)-5-(4-nitro-phenyl)-2-oxo-2,5-dihydro-pyrrol-1-yl]-hexanoic acid hydroxyamide | 471.18 | 471.18 | 493.16 | 493.19 |
| 2-[2-(1-ethyl-propyl)-4-hydroxy-3-(3-hydroxy-phenyl)-5-oxo-2,5-dihydro-pyrrol-1-yl]-hexanoic acid hydroxyamide | 391.27 | 391.33 | 413.26 | 413.31 |
| 2-[3-hydroxy-5-(2-methylsulfanyl-ethyl)-4-(2-nitro-phenyl)-2-oxo-2,5-dihydro-pyrrol-1-yl]-hexanoic acid hydroxyamide | 424.19 | 424.2 | 446.18 | 446.19 |
| 2-[3-hydroxy-4-(2-nitro-phenyl)-2-oxo-5-o-tolyl-2,5-dihydro-pyrrol-1-yl]-hexanoic acid hydroxyamide | 440.22 | 440.22 | 462.2 | 462.2 | n.d. = not detected

What I claim is:

1. A compound of formula (I)

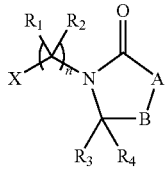

(I)

wherein the radicals $R_1$ and $R_2$, independently of one another, are a hydrogen atom, or an $C_1$-$C_{12}$ alkyl, $C_2$-$C_{12}$ alkenyl, $C_2$-$C_{12}$ alkynyl, $C_1$-$C_{12}$ heteroalkyl, aryl, having 6 to 10 ring carbon atoms, heteroaryl, having 5 to 10 ring atoms and one or more oxygen, nitrogen, phosphorus, or sulphur ring atoms, $C_3$-$C_7$ cycloalkyl, $C_1$$C_6$ alkyl$C_3$-$C_7$cycloalkyl, $C_1$$C_6$heteroalkyl$C_3$-$C_7$cycloalkyl, heterocycloalkyl, having 3 to 7 ring atoms and one or more oxygen, nitrogen or sulphur ring atoms, aralkyl having 7 to 16 carbon atoms or heteroaralkyl having 7 to 16 carbon, nitrogen, oxygen or sulphur atoms of which 1 to 4 atoms are nitrogen, oxygen or sulfur; and $R_3$ is a hydrogen atom, or an $C_1$-$C_{12}$ alkyl, $C_2$-$C_{12}$ alkenyl, $C_2$-$C_{12}$ alkenyl, $C_1$-$C_{12}$ heteroalkyl, aryl having 6 to 10 ring carbon atoms, heteroaryl having 5 to 10 ring atoms and one or more oxygen, nitrogen, phosphorus, or sulphur ring atoms, $C_3$-$C_7$cycloalkyl, $C_1$-$C_6$alkyl$C_3$-$C_7$cycloalkyl, $C_1$-$C_6$heteroalkyl$C_3$-$C_7$cycloalkyl, heterocycloalkyl having 3 to 7 ring atoms and one or more oxygen, nitrogen or sulphur ring atoms, aralkyl having 7 to 16 carbon atoms or heteroaralkyl having 7 to 16 carbon, nitrogen, oxygen or sulphur atoms of which 1 to 4 atoms are nitrogen, oxygen or sulfur;

$R_4$ is a hydrogen atom, or an $C_1$-$C_{12}$ alkyl, $C_2$-$C_{12}$ alkenyl, $C_2$-$C_{12}$ alkenyl, $C_1$-$C_{12}$ heteroalkyl, aryl having 6 to 10 ring carbon atoms, heteroaryl having 5 to 10 ring atoms and one or more oxygen, nitrogen, phosphorus, or sulphur ring atoms, $C_3$-$C_7$ cycloalkyl, $C_1$-$C_6$alkyl$C_3$-$C_7$cycloalkyl, $C_1$-$C_6$heteroalkyl$C_3$-$C_7$cycloalkyl, heterocycloalkyl having 3 to 7 ring atoms and one or more oxygen, nitrogen or sulphur ring atoms, aralkyl having 7 to 16 carbon atoms or heteroaralkyl having 7 to 16 carbon, nitrogen, oxygen or sulphur atoms of which 1 to 4 atoms are nitrogen, oxygen or sulfur;

n is equal to 1 or 2;

A-B together is a group of formula —C(OR$_6$)=CR$_5$—;

$R_5$ is a hydrogen atom, a halogen atom, or an $C_1$-$C_{12}$ alkyl, $C_2$-$C_{12}$ alkenyl, $C_2$-$C_{12}$ alkynyl, $C_1$-$C_{12}$ heteroalkyl, aryl having 6 to 10 ring carbon atoms, heteroaryl having 5 to 10 ring atoms and one or more oxygen, nitrogen, phosphorus, or sulphur ring atoms, $C_3$-$C_7$ cycloalkyl, $C_1$-$C_6$alkyl$C_3$-$C_7$cycloalkyl, $C_1$-$C_6$heteroalkyl$C_3$-$C_7$cycloalkyl, heterocycloalkyl having 3 to 7 ring atoms and one or more oxygen, nitrogen or sulphur ring atoms, aralkyl having 7 to 16 carbon atoms or heteroaralkyl having 7 to 16 carbon, nitrogen, oxygen or sulphur atoms of which 1 to 4 atoms are nitrogen, oxygen or sulfur;

$R_6$ is a hydrogen atom, or an $C_1$-$C_{12}$ alkyl, $C_2$-$C_{12}$ alkenyl, $C_2$-$C_{12}$ alkynyl, $C_1$-$C_{12}$ heteroalkyl, aryl having 6 to 10 ring carbon atoms, heteroaryl having 5 to 10 ring atoms and one or more oxygen, nitrogen, phosphorus, or sulphur ring atoms, $C_3$-$C_7$ cycloalkyl, $C_1$-$C_6$alkyl$C_3$-$C_7$cycloalkyl, $C_1$-$C_6$heteroalkyl$C_3$-$C_7$cycloalkyl, heterocycloalkyl having 3 to 7 ring atoms and one or more oxygen, nitrogen or sulphur ring atoms, aralkyl having 7 to 16 carbon atoms or heteroaralkyl having 7 to 16 carbon, nitrogen, oxygen or sulphur atoms of which 1 to 4 atoms are nitrogen, oxygen or sulfur;

$R_7$ is a hydrogen atom, or an $C_1$-$C_{12}$ alkyl, $C_2$-$C_{12}$ alkenyl, $C_2$-$C_{12}$ alkynyl, $C_1$-$C_{12}$ heteroalkyl, aryl having 6 to 10 ring carbon atoms, heteroaryl having 5 to 10 ring atoms and one or more oxygen, nitrogen, phosphorus, or sulphur ring atoms, $C_3$-$C_7$ cycloalkyl, $C_1$-$C_6$alkyl$C_3$-$C_7$cycloalkyl, $C_1$-$C_6$heteroalkyl$C_3$-$C_7$cycloalkyl, heterocycloalkyl having 3 to 7 ring atoms and one or more oxygen, nitrogen or sulphur ring atoms, aralkyl having 7 to 16 carbon atoms or heteroaralkyl having 7 to 16 carbon, nitrogen, oxygen or sulphur atoms of which 1 to 4 atoms are nitrogen, oxygen or sulfur;

X is a group of formula:

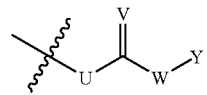

whereby U is a bond, V is O, S, NH or $CH_2$, W is O, S, NH or $CH_2$, and Y is OH or $NH_2$ whereby each aryl or heteroaryl is unsubstituted or substituted with one or more fluorine, chlorine, bromine, iodine, —COOH, —OH, —SH, —$NH_2$ or —$NO_2$ groups, and, whereby compounds of formula (I), in which $R_5$ is a group of formula -Q (=O)-$R_8$ are excluded, whereby Q is a sulfur atom, a carbon atom or a S=O group, and $R_8$ is a hydrogen atom, a halogen atom, an alkyl, alkenyl, alkinyl, heteroalkyl, aryl, heteroaryl, cycloalkyl, alkylcycloalkyl, heteroalkylcycloalkyl, heterocycloalkyl, aralkyl or a heteroaralkyl radical;

or a pharmaceutically acceptable salt, or a pharmaceutically acceptable formulation thereof.

2. The compound according to claim 1, whereby X is a group of formula —CO—NHOH.

3. The compound according to claim 1, whereby $R_1$ is a hydrogen atom.

4. The compound according to claim 1, whereby $R_2$ is a $C_{3-7}$-alkyl or $C_{3-7}$-heteroalkyl group.

5. The compound according to claim 1, whereby $R_2$ is a n-butyl or n-pentyl group.

6. The compound according to claim 1, whereby $R_3$ is a hydrogen atom.

7. The compound according to claim 1, whereby $R_5$ is a propyl, isopropyl, phenyl, o-nitrophenyl, p-hydroxyphenyl, m-hydroxyphenyl, m,p-dihydroxyphenyl, or 3'-indolyl group.

8. The compound according to claim 1, whereby the radicals $R_6$ and $R_7$ are hydrogen atoms.

9. The compound according to claim 1, whereby n is equal to 1.

10. A pharmaceutical composition which contains a compound according to claim 1 and optionally carriers and/or adjuvants.

\* \* \* \* \*